United States Patent [19]
DeYoung et al.

[11] Patent Number: 6,090,781
[45] Date of Patent: Jul. 18, 2000

[54] STABILIZING FORMULATION FOR NGF

[75] Inventors: Linda R. DeYoung, El Granada; Xanthe M. Lam, Daly City; Tue H. Nguyen, San Mateo; Michael F. Powell, San Francisco, all of Calif.

[73] Assignee: Genentech, Inc., South San Francisco, Calif.

[21] Appl. No.: 08/746,073

[22] Filed: Nov. 6, 1996

Related U.S. Application Data

[60] Provisional application No. 60/046,874, Nov. 7, 1995.

[51] Int. Cl.$^7$ ..................................................... A61K 38/18
[52] U.S. Cl. ............................................. 514/12; 530/399
[58] Field of Search ................................. 514/12; 530/399

[56] References Cited

U.S. PATENT DOCUMENTS

| | | |
|---|---|---|
| 5,082,774 | 1/1992 | Heinrich . |
| 5,210,185 | 5/1993 | Della Valle et al. . |
| 5,457,034 | 10/1995 | Della Valle et al. . |
| 5,763,394 | 6/1998 | O'Connor et al. . |

FOREIGN PATENT DOCUMENTS

| | | | |
|---|---|---|---|
| WO 94/26302 | 11/1994 | WIPO | ............................ A61K 37/66 |
| WO 95/05845 | 3/1995 | WIPO | ............................ A61K 38/18 |

OTHER PUBLICATIONS

Apfel et al., "Never Growth Factor Prevents Experimental Cisplatin Neuropathy" *Ann. Neurol.* 31:76–80 (1992).
Bothwell et al., "Dissociation Equilibrium Constant of β Nerve Growth Factor" *The Journal of Biological Chemistry* 252 (23) :8532–8536 (Dec. 10, 1977).
Canova–Davis et al., "Amino–terminal Serine to Glycine Post–translational Modification Observed in Nerve Growth Factor Biosynthesized in Chinese Hamster Ovary Cells" *Analytical Methods* pp. 230–231.
De Young et al., "Temperature and PH Dependence of Recombinant Human Nerve Growth Factor Dimer Dissociation" *Biophys. Journal* 66(2) :A401 (Feb. 1994).
Greene, "A Quantitative Bioassay for Nerve Growth Factor (NGF) Activity Employing a Clonal Pheochromocytoma Cell Line" *Brain Research* 133:350–353 (1977).
McDonald et al., "New Protein Fold Revealed by a 2.3–A Resolution Crystal Structure of Nerve Growth Factor" *Nature* 354:411–414 (1991).
Moore et al., "The Use of Hybrid Molecules in a Study of the Equilibrium Between Nerve Growth Factor Monomers and Dimers" *Neurobiology* 5:369–381 (1975).
Petty et al., "The Effect of Systematically Administered Recombinant Human Nerve Growth Factor in Healthy Human Subjects" *Ann. Neurol.* 36:244–246 (1994).
Reed et al., "Lysis of Human Red Blood Cells in the Presence of Various Cosolvents. III. The Relationship Between Hemolytic Potential and Structure" *Journal of Parenteral Science & Technology* 41(1):37–39 (Feb. 1987).
Schmelzer et al., "Biochemical Characterization of Recombinant Human Nerve Growth Factor" *Journal of Neurochemistry* 59(5) :1675–1683 (1992).
Thoenen et al., "Physiology of Nerve Growth Factor" *Physiological Reviews* 60(4) :1284–1335 (Oct. 1980).
Timm et al., "Comparitive Equilibrium Denaturation Studies of the Neurotrophins: Nerve Growth Factor, Brain–derived Neurotrophic Factor, Neurotrophin 3, and Neurotrophin 4/5" *Biochemistry* 33:4667–4676 (1994).
Timm et al., "Equilibrium Denaturation Studies of Mouse β–nerve Growth Factor" *Protein Science* I:236–244 (1992).
Calbiochem 1994/1995 Product Catalog, p. 233.
Apfel, S.C. et al., *Ann. Neurol.*, 29:87–90, 1991.
*Remington's Pharmaceutical Sciences*, 18$^{th}$ Edition, Mack Publishing Co.; Easton, PA, 1990, pp. 1056, 1286, 1449.

*Primary Examiner*—Marianne P. Allen
*Attorney, Agent, or Firm*—Knobbe, Martens, Olson & Bear, LLP

[57] ABSTRACT

Formulations are provided comprising NGF and acetate-containing buffer from pH 5 to 6 that provide enhanced stability of NGF for use in promoting nerve cell growth, repair, survival, differentiation, maturation or function.

1 Claim, 17 Drawing Sheets a = di-oxidized rhNGF
b = deamidated rhNGF
c = mono-oxidized rhNGF
d = Iso-aspartate
e = 120 rh NGF f = 118 rhNGF
g = N-terminal clipping
h = misfolded rhNGF
i = protein eluted at gradient ramp a: Mono- & di-oxidized 118/118 and oxidized N-terminally clipped rhNGF
b: 118/118 rhNGF homodimer
c: Ser-Gly 118/118 rhNGF (1-chain)

STABILIZING FORMULATION FOR NGF

This application claims the benefit of U.S. provisional application no. 60/046,874, having an effective filing date of Nov. 7, 1995, as properly and timely obtained by the petition dated Nov. 5, 1996, under 37 CFR §1.53(b)(2)(ii) from U.S. Ser. No. 08/554,685, filed Nov. 7, 1995, the contents of which are incorporated herein by reference.

BACKGROUND

1. Field of the Invention

This invention relates to formulations of nerve growth factor ("NGF") and their use to induce nerve cell growth, differentiation, survival, repair, maturation, or function in vivo or ex vivo. More particularly, this invention relates to such pharmaceutical compositions having increased stability and solubility characteristics for the NGF component, particularly human recombinant NGF ("rhNGF"), and those making possible the ability to create stable forms thereof for safe, effective therapeutic administration to human subjects.

2. Description of Related Disclosures

Nerve growth factor (NGF) is a neurotrophic factor required for the growth and survival of sympathetic and sensory neurons during development and in mature animals (1). Clinical indications for recombinant human NGF include peripheral sensory neuropathy and Alzheimer's disease. For example, the systemic administration of NGF has been shown to reduce the sensory neuropathy induced by administration of cisplatin and taxol to mice (2,3). In recent clinical trials, NGF has been administered to humans to improve sensory function in diabetic neuropathies (4).

NGF is currently being developed as a liquid parenteral formulation. The protein stability is complicated beyond the usual chemical and physical degradation pathways due to the dimeric structure of NGF. Protein stability can be further complicated when recombinant protein is a mixture of C-terminally clipped NGF variants. The crystal structure of murine NGF shows 3 antiparallel pairs of b-strands forming a flat surface through which the monomers dimerize (5); the dimer dissociation constant is $\leq 10^{-13}$ M (6,7). The rearrangement of monomers within dimers, towards an equilibrium dimer distribution, complicates quantification of NGF dimer degradation.

There exists a need for formulations containing NGF that lead to NGF stability while being safe and effective for therapeutic administration to mammals, particularly human subjects.

SUMMARY

The present invention is based on the finding of formulation conditions and methods for stability of NGF in a liquid formulation. It is an object of the present invention to provide a suitable formulation of NGF with enhanced stability of NGF to provide effective induction of nerve cell growth, survival, differentiation, maturation, repair, or function, preferably in vivo or ex vivo. In various embodiments the formulations can have enhanced stability to agitation, freezing, thawing, light, or storage. It is another object of the invention to provide a stable NGF formulation for use in treating a mammal, preferably human, in need of NGF treatment so as to provide a therapeutically effective amount of NGF. It is further object to provide an NGF formulation with enhanced consistency for improved application to the neuron or mammal. These and other objects will become apparent to those skilled in the art.

The above objects are achieved by providing an NGF formulation comprising an effective amount of NGF in a pharmaceutically acceptable acetate buffer, preferably sodium acetate. In a specific embodiment this formulation contains about 0.1 to 2.0 mg/ml NGF in an acetate buffer from 5 to 50 mM, from pH 5 to 6. The formulation can optionally contain a pharmaceutically acceptable diluent, a pharmaceutically acceptable salt, preferably sodium chloride, or a preservative, preferably benzyl alcohol.

In another embodiment the invention provides a method of producing an NGF formulation produced by the steps including formulating NGF and acetate, and optionally sodium chloride, and further optionally a preservative.

In another embodiment a method is presented by which NGF dimer degradation is quantitated independent of dimer exchange.

DETAILED DESCRIPTION

Figure 1:
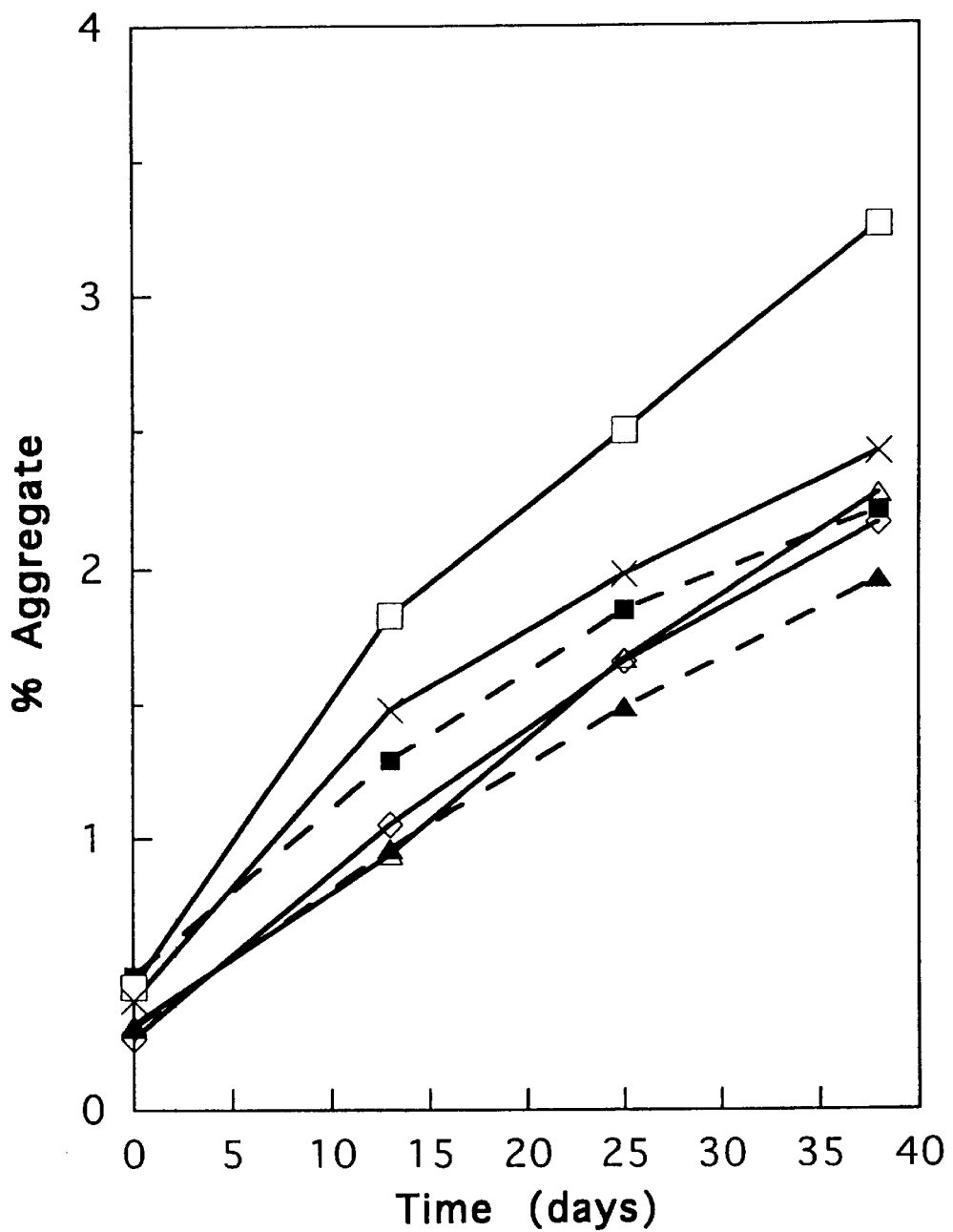
FIG. 1 depicts the dependence of NGF aggregate formation at 37° C. on formulation buffer and pH, quantitated by size-exclusion chromatography, (◇) succinate pH 4.2; (Δ) succinate pH 5.0; (□) succinate pH 5.8; (X) succinate pH 5.0 with 0.05% Tween 20; (▲) acetate pH 5.0; and (■) acetate pH 5.8.

The present invention is based on the discovery that NGF formulated in pharmaceutically acceptable acetate buffer from pH 5 to pH 6 as a pharmaceutical composition has markedly increased stability in these compositions. Acetate concentrations can range from 0.1 to 200 mM, more preferably from 1 to 50 mM, and even more 5 to 30 mM, and most preferably from 10 to 20 mM. One preferred embodiment has 20 mM acetate and another has 10 mM acetate in the administered solution. A preferred acetate salt for enhancing stability and buffering capacity is sodium acetate. However other physiologically acceptable acetate salts can be used, for example potassium acetate. Suitable pH ranges for the preparation of the compositions herein are from 5 to 6, preferably 5.4 to 5.9, more preferably 5.5 to 5.8. A preferred pH is 5.5 which enhances stability and buffering capacity. Another preferred embodiment is pH 5.8.

A "pharmaceutically effective amount" of NGF refers to that amount which provides therapeutic effect in various administration regimens. The compositions herein are prepared containing amounts of NGF from 0.07 to 20 mg/ml, preferably 0.08 to 15 mg/ml, more preferably 0.09 to 10 mg/ml, and most preferably 0.1 to 2 mg/ml. In a preferred embodiment the NGF concentration is 0.1 mg/ml. In another preferred embodiment the NGF concentration is 2.0 mg/ml. For use of these compositions in administration to human patients suffering from peripheral neuropathies, for example, these compositions may contain from about 0.1 mg/ml to about 2 mg/ml NGF, corresponding to the currently contemplated dosage rate for such treatment. NGF is well-tolerated and higher doses can be administered if necessary as determined by the physician.

Optionally, but preferably, the formulation contains a pharmaceutically acceptable salt, preferably sodium chloride, and preferably at about physiological concentrations. Low concentrations are preferred, e.g., less than about 0.3 M to about 0.05 M, preferably from 0.16 to 0.20 M NaCl, more preferably 0.13 to 0.15 M. In a preferred embodiment the sodium chloride concentration is 136 mM. In another preferred embodiment the concentration is 142 mM.

Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Benzyl alcohol is a particularly preferred preservative that results in enhanced NGF stability. A particularly preferred benzyl alcohol concentration is 0.7 to 1.2%, more preferably 0.8 to 1.0%, with a particularly preferred concentration of 0.9%.

Optionally, the formulations of the invention can include a pharmaceutically acceptable surfactant. Preferred surfactants are non-ionic detergents. Preferred surfactants include Tween 20 and pluronic acid (F68). F68 is particularly preferred for enhancing NGF stability. Suitable surfactant concentrations are 0.005 to 0.02%. A preferred concentration for surfactant is 0.01%. Surfactants are used to minimize particulate formation.

In a particularly preferred embodiment the composition contains an NGF concentration of 0.1 mg/ml, a sodium acetate concentration of 20 mM, pH 5.5, a sodium chloride concentration of 136 mM, and benzyl alcohol concentration at 0.9% (v/v). In another embodiment the NGF concentration is 2.0 mg/ml, the sodium acetate concentration is 10 mM, pH 5.5, and the sodium chloride concentration is 142 mM.

In another embodiment of the invention is provided a kit for NGF administration, which includes a vial or receptacle containing a pharmaceutical composition of the invention comprising a pharmaceutically effective amount of nerve growth factor and a pharmaceutically acceptable acetate-containing buffer. A preferred vial volume is one suitable for multi-dose use—allowing repeated withdrawal of sample. The increased stability attained with the formulations of the invention allow multi-dose liquid formulation. Typically a multi-dose vial will provide sufficient formulation to supply sufficient dosage for one patient for one month, preferably one week. For example, the composition volume generally ranges from 0.3 to 10.0 ml and more preferably from 1.6 to 2.0 ml, depending on dose concentration, frequency and ease of use. For example, a volume of 1.8 ml is convenient when either 0.3 ug/kg or 0.1 ug/kg are used, allowing 7 or 24 doses, respectively. When a light sensitive component, such as benzyl alcohol is present, the vial is protected from intense light. Generally it is sufficient to store the vial in a darkened refrigerator or within an opaque box. However, the vial walls can comprise light transmission reducing materials. For example, translucent amber or brown vials or an opaque vail can be used. In preferred embodiments the vial contains multi-dose formulation. For a vial configuration, a selected multi-dose liquid formulation can be filled in 3 cc Type I glass vial with 1.8 mL fill volume. Selection of stopper will be based on compatibility of different types of stopper with the selected formulation.

Compositions of the invention are typically stored at 2 to 8 degrees C. The formulations are stable to numerous freeze thaw cycles as shown herein.

In another embodiment the formulation is prepared with the above acetate concentrations.

A preferred means of preparing a formulation is to dialyze a bulk NGF solution into the final formulation buffer. Final NGF concentrations are achieved by appropriate adjustment of the formulation with formulation buffer absent NGF. Also provided are methods for the preparation of the composition of claim 1 comprising the steps of compounding said NGF and acetate-containing buffer. Also provided are methods of increasing the stability of NGF in a pharmaceutical composition containing NGF as active principle, comprising incorporating acetate in said composition, wherein said acetate is present in an amount and pH effective to increase the stability of the NGF.

The compositions hereof including lyophilized forms, are prepared in general by compounding the components using generally available pharmaceutical compounding techniques, known per se. Likewise, standard lyophilization procedures and equipment well-known in the art are employed. A particular method for preparing a pharmaceutical composition of NGF hereof comprises employing purified (according to any standard protein purification scheme) NGF, preferably rhNGF, in any one of several known buffer exchange methods, such as gel filtration or dialysis.

Nerve growth factor ("NGF") is a 120 amino acid polypeptide homodimeric protein that has prominent effects on developing sensory and sympathetic neurons of the peripheral nervous system. NGF acts via specific cell surface receptors on responsive neurons to support neuronal survival, promote neurite outgrowth, and enhance neurochemical differentiation. NGF actions are accompanied by alterations in neuronal membranes, in the state of phosphorylation of neuronal proteins, and in the abundance of certain mRNAs and proteins likely to play a role in neuronal differentiation and fiction. (Connolly et al., J. Cell. Biol. 90:176–180 [1981]; Skaper and Varon, Brain Res. 197:379–389 [1980]; Yu, et al., J. Biol. Chem. 255:10481–10492 [1980]; Haleqoua and Patrick, Cell 22:571–581 [1980]; Tiercy and Shooter, J. Cell. Biol. 103:2367–2378 [1986]).

Forebrain cholinergic neurons also respond to NGF and may require NGF for trophic support. (Hefti, J. Neurosci. 6:2155 [1986]). Indeed, the distribution and ontogenesis of NGF and its receptor in the central nervous system (CNS) suggest that NGF acts as a target-derived neurotrophic factor for basal forebrain cholinergic neurons (Korsching, TINS, pp 570–573 [November/December 1986]).

Little is known about the NGF amino acid residues necessary for the interaction with the trkA-tyrosine kinase receptor. Significant losses of biological activity and receptor binding were observed with purified homodimers of human and mouse NGF, representing homogenous truncated forms modified at the amino and carboxy termini. The 109 amino acid species (10–118)hNGF, resulting from the loss of the first 9 residues of the N-terminus and the last two residues from the C-terminus of purified recombinant human NGF, is 300-fold less efficient in displacing mouse [$^{125}$I] NGF from the human trkA receptor compared to (1–118) hNGF. It is 50- to 100-fold less active in dorsal root ganglion and sympathetic ganglion survival compared to (1–118) hNGF. The (1–118)hNGF has considerably lower trkA tyrosine kinase autophosphorylation activity. A preferred form is the 118 amino acid human NGF, which is more preferable as a homodimer.

The formulations of the invention include the pantropic neurotrophin pantropic NGF. Pantropic NGF is a pantropic neurotrophin which has an amino acid sequence homologous to the amino acid sequence of NGF, with domains which confer other neurotrophin specificities. In the preferred embodiment, the domains are substituted for NGF residues; that is, some number of amino acids are deleted from the NGF sequence, and an identical or similar number of amino acids are substituted, conferring an additional specificity. For example, a pantropic NGF is made with a D16A substitution, which confers BDNF specificity. Optionally, substitutions in the pre-variable region 1 (V18E+V20L+G23T) and in variable region 4 (Y79Q+ T81K+H84Q+F86Y+K88R) are included. Alternatively, the substitutions in the pre-variable region 1 can be made with only single amino acid substitutions in variable region 4; for example, V18E+V20L+G23T and one of Y79Q, T81K, H84Q, F86Y, or K88R may be made.

The chemical and physical stability of recombinant human nerve growth factor (NGF) in aqueous solution was investigated between 5 and 37° C., in the pH range 4.2 to 5.8. NGF chemical stability increased with increasing pH. In succinate buffer at pH 5.8, NGF physical stability decreased due to protein aggregation. Based on both the 5° C. stability data and accelerated degradation studies at 37° C., the optimal formulation was found to be acetate buffer at pH 5.8. Reversed-phase HPLC was the primary stability indicating method, showing conversion of Asn-93 to iso-Asp to be the primary degradation pathway at 5° C. Quantitation of NGF degradation by cation exchange chromatography was complicated by the rearrangement of the NGF monomer variants into various mixed dimers over time (dimer exchange). Treatment of samples and controls with dilute acid rapidly equilibrated the monomer distribution in the dimers, allowing NGF degradation to be quantitated in the absence of dimer exchange.

Benzyl alcohol and phenol were evaluated for their compatibility and stability with rhNGF in two liquid formulations for multi-use purposes. These two formulations consist of 0.1 mg/mL protein in 20 mM sodium acetate at pH 5.5 and 136 mM sodium chloride with and without 0.01% pluronic acid (F68) as surfactant. The final concentrations of benzyl alcohol and phenol in each of these two formulations were 0.9 and 0.25%, respectively. Based on the 12 month stability data, rhNGF is more stable with benzyl alcohol than phenol in these formulations. Benzyl alcohol preserved rhNGF formulation with the presence of surfactant is as stable as the formulation with no surfactant added, indicating that the addition of F68 to rhNGF multi-dose formulation is not required for stability purpose. Therefore, a formulation consisting of 0.1 mg/mL protein in 20 mM acetate, 136 mM NaCl, 0.9% benzyl alcohol, pH 5.5 is recommended for rhNGF used for multiple dosing in Phase III clinical trails. This rhNGF multi-dose formulation passed the USP and EP preservative efficacy test after 6 months at 5 degrees C., and is as stable as the current liquid formulation at 2 mg/mL. However, the formulation should avoid exposure to intensive light due to the presence of benzyl alcohol as preservative which is light sensitive.

In general, the compositions may contain other components in amounts preferably not detracting from the preparation of stable, liquid or lyophilizable forms and in amounts suitable for effective, safe pharmaceutical administration.

In order that materials like NGF be provided to health care personnel and patients, these materials must be prepared as pharmaceutical compositions. Such compositions must be stable for appropriate periods of time, must be acceptable in their own right for administration to humans, and must be readily manufacturable. An example of such a composition would be a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the medicinal agent contained in the composition under a wider variety of storage conditions, as it is recognized by those skilled in the art that lyophilized preparations are generally more stable than their liquid counterparts. Such lyophilized preparations are reconstituted prior to use by the addition of suitable pharmaceutically acceptable diluent(s), such as sterile water for injection or sterile physiological saline solution, and the like.

NGF formulations of the invention are believed to be useful in promoting the development, maintenance, or regeneration of neurons in vivo, including central (brain and spinal chord), peripheral (sympathetic, parasympathetic, sensory, and enteric neurons), and motorneurons. Accordingly, NGF formulations of the invention are utilized in methods for the treatment of a variety of neurologic diseases and disorders. In a preferred embodiment, the formulations of the present invention are administered to a patient to treat neural disorders. By "neural disorders" herein is meant disorders of the central and/or peripheral nervous system that are associated with neuron degeneration or damage. Specific examples of neural disorders include, but are not limited to, Alzheimer's disease, Parkinson's disease, Huntington's chorea, stroke, ALS, peripheral neuropathies, and other conditions characterized by necrosis or loss of neurons, whether central, peripheral, or motorneurons, in addition to treating damaged nerves due to trauma, burns, kidney disfunction, injury, and the toxic effects of chemotherapeutics used to treat cancer and AIDS. For example, peripheral neuropathies associated with certain conditions, such as neuropathies associated with diabetes, AIDS, or chemotherapy may be treated using the formulations of the present invention. It also is useful as a component of culture media for use in culturing nerve cells in vitro or ex vivo.

In various embodiments of the invention, NGF formulations are administered to patients in whom the nervous system has been damaged by trauma, surgery, stroke, ischemia, infection, metabolic disease, nutritional deficiency, malignancy, or toxic agents, to promote the survival or growth of neurons, or in whatever conditions have been found treatable with NGF. For example, NGF formulation of the invention can be used to promote the survival or growth of motorneurons that are damaged by trauma or surgery. Also, NGF formulations of the invention can be used to treat motoneuron disorders, such as amyotrophic lateral sclerosis (Lou Gehrig's disease), Bell's palsy, and various conditions involving spinal muscular atrophy, or paralysis. NGF formulations of the invention can be used to treat human neurodegenerative disorders, such as Alzheimer's disease, Parkinson's disease, epilepsy, multiple sclerosis, Huntington's chorea, Down's Syndrome, nerve deafness, and Meniere's disease. NGF formulations of the invention can be used as cognitive enhancer, to enhance learning particularly in dementias or trauma. Alzheimer's disease, which has been identified by the National Institutes of Aging as accounting for more than 50% of dementia in the elderly, is also the fourth or fifth leading cause of death in Americans over 65 years of age. Four million Americans, 40% of Americans over age 85 (the fastest growing segment of the U.S. population), have Alzheimer's disease. Twenty-five percent of all patients with Parkinson's disease also suffer from Alzheimer's disease-like dementia. And in about 15% of patients with dementia, Alzheimer's disease and multi-infarct dementia coexist. The third most common cause of dementia, after Alzheimer's disease and vascular dementia, is cognitive impairment due to organic brain disease related directly to alcoholism, which occurs in about 10% of alcoholics. However, the most consistent abnormality for Alzheimer's disease, as well as for vascular dementia and cognitive impairment due to organic brain disease related to alcoholism, is the degeneration of the cholinergic system arising from the basal forebrain (BF) to both the codex and hippocampus (Bigl et al. in *Brain Cholinergic Systems,* M. Steriade and D. Biesold, eds., Oxford University Press, Oxford, pp. 364–386 (1990)). And there are a number of other neurotransmitter systems affected by Alzheimer's disease (Davies *Med. Res. Rev.* 3:221 (1983)). However, cognitive impairment, related for example to degeneration of the cholinergic neurotransmitter system, is not limited to individuals suffering from dementia. It has also been seen in otherwise healthy aged adults and rats. Studies that compare the degree of learning impairment with the degree of reduced cortical cerebral blood flow in aged rats show a good correlation (Berman et al. *Neurobiol. Aging* 9:691 (1988)). In chronic alcoholism the resultant organic brain disease, like Alzheimer's disease and normal aging, is also characterized by diffuse reductions in cortical cerebral blood flow in those brain regions where cholinergic neurons arise (basal forebrain) and to which they project (cerebral cortex) (Lofti et al., *Cerebrovasc. and Brain Metab. Rev* 1:2 (1989)). Such dementias can be treated by administration of NGF formulations of the invention.

Further, NGF formulations of the invention are preferably used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to diabetic peripheral neuropathy, distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent such as vincristine, cisplatin, methotrexate, or 3'-azido-3'-deoxythymidine.

A therapeutically effective dose of an NGF formulation is administered to a patient. By "therapeutically effective dose" herein is meant a dose that produces the effects for which it is administered. The exact dose will depend on the disorder to be treated, and will be ascertainable by one skilled in the art using known techniques. In general, the NGF formulations of the present invention are administered at about 0.01 μg/kg to about 100 mg/kg per day. Preferably, from 0.1 to 0.3 ug/kg. In addition, as is known in the art, adjustments for age as well as the body weight, general health, sex, diet, time of administration, drug interaction and the severity of the disease may be necessary, and will be ascertainable with routine experimentation by those skilled in the art. Typically, the clinician will administer NGF formulations of the invention until a dosage is reached that repairs, maintains, and, optimally, reestablishes neuron function. The progress of this therapy is easily monitored by conventional assays.

A "patient" for the purposes of the present invention includes both humans and other mammals. Thus the methods are applicable to both human therapy and veterinary applications.

Therapeutic formulations of NGF are prepared by mixing NGF having the desired degree of purity with optional physiologically acceptable carriers, excipients or stabilizers (*Remington's Pharmaceutical Sciences*). Acceptable carriers, excipients or stabilizers are nontoxic to recipients at the dosages and concentrations employed and will not significantly decrease NGF stability in the formulations as taught herein. Such compounds include antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as histidine, methionine, glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or non-ionic surfactants such as Tween, Pluronics or PEG.

NGF formulations to be used for in vivo administration must be sterile. This is readily accomplished by filtration through sterile filtration membranes. Ordinarily NGF formulations of the present invention will be stored in liquid form at 2 to 8 degrees C. The formulations are suitable for frozen storage with repeated cycles of thawing and freezing.

Therapeutic NGF compositions generally are placed into a container having a sterile access port, for example, an intravenous solution bag or vial having a stopper pierceable by a hypodermic injection needle.

NGF optionally is combined with or administered in concert with other neurotrophic factors including NT-4/5, NT-3, and/or BDNF and is used with other conventional therapies for nerve disorders.

The administration of the formulations of the present invention can be done in a variety of ways, including, but not limited to, orally, subcutaneously, intravenously, intracerebrally, intranasally, transdermally, intraperitoneally, intramuscularly, intrapulmonary, vaginally, rectally, or intraocularly. The formulations can be administered continuously by infusion into the fluid reservoirs of the CNS, although bolus injection is acceptable, using techniques well known in the art, such as pumps or implantation. In some instances, for example, in the treatment of wounds, the formulations may be directly applied as a solution or spray.

The following examples are offered by way of illustration and not by way of limitation. The disclosures of all citations in the specification are expressly incorporated herein by reference.

EXAMPLES

Example I

Materials

Recombinant human nerve growth factor (NGF) was produced in Chinese hamster ovary cells and purified by reversed-phase (RP-HPLC) and ion-exchange chromatography (IEC) as described previously (8). HPLC grade acetonitrile, and TFA were used for RP-HPLC. All other chemicals were USP grade. Sterile type I, clear glass, 2 cc vials were purchased from Wheaton and used with siliconized, Teflon-coated, butyl rubber stoppers.

Methods

NGF was dialyzed into 10 mM sodium acetate, 142 mM sodium chloride, at pH 5.0 and 5.8, and into 10 mM sodium succinate, 142 mM NaCl, at pH 4.2, 5.0, and 5.8, and adjusted to 10 mg/ml. Tween 20 was also added to a succinate pH 5.0 formulation to determine if surfactant would reduce NGF aggregation (10 mM sodium succinate, 142 mM NaCl, 0.05% Tween 20).

Vials were aseptically filled with 0.3 ml of NGF formulation and stored at 5, 25, and 37° C. (25° C. data not reported here). Controls were stored at −70° C. where no significant degradation has been observed. At each time point, 50 μl aliquots were removed from individual vials and stored at −70° C. until analysis.

HPLC Analysis

Cation exchange HPLC (IEC) was carried out on a HP 1090 system using a Tosohas sulpho-propyl TSK-SP-5PW (7.5×75 mm) column with 10 m particles. Mobile phases were (A) 10 mM sodium phosphate, 5% (v/v) acetonitrile, pH 7.0 and (B) A+1.0 M ammonium chloride. NGF was eluted at 35° C. (0.5 ml/min) with a linear gradient of 20–40% B from 5 to 60 minutes. The control and 1.6 year samples at 5° C. were also assayed after "acid-treatment" to bring the distribution of monomer variants in the dimers to equilibrium (8, 9). These samples were adjusted to pH 3.5 with HCl and incubated at 37° C. for 2 hours (results at 2 and 4 hours were equivalent). A YMC C4, 5 μm (4.6×250 mm) column was used for reversed-phase HPLC (RP-HPLC) on a HP 1090 system at 25° C. NGF was eluted (0.5 ml/min) using a linear gradient of 26–30% B in A (B=0.05% TFA in acetonitrile and A=0.05% TFA in water) run between 5 and 40 minutes. Size exclusion HPLC ("SEC-HPLC") was carried out using a Perkin Elmer Series 410 Bio LC Pump with a Perkin Elmer LC 90 Spectrophotometric UV Detector and a Tosohas TSK 2000 SWXL, 5 μm (7.8×300 mm) column. This SEC column was run at 0.5 ml/min using a 0.2 M potassium phosphate, 0.45 M potassium chloride mobile phase, at pH 7.0. For SEC UV detection was at 280 nm; for RP-HPLC and IEC, at 214 nm. For all assays 50 mg of NGF were injected.

SDS-PAGE

Samples were diluted into Novex tricine SDS sample buffer and incubated for 1 hour at 50° C. Non-reduced SDS-PAGE was run on Novex tricine gels containing 10% acrylamide followed by Coomassie Blue staining. Molecular weights were estimated using Bio-Rad low molecular weight markers. Neurite Outgrowth Assay. The biological activity of NGF was determined using the PC12 assay developed by Greene (10) and modified as described by Schmelzer et al (8).

Hemolysis

All formulations were tested for hemolytic activity. The hemolysis procedure was that of Reed and Yalkowsky (11) except that equal volumes of washed human red blood cells and formulation were incubated at 37° C. for 30 minutes before analysis.

Results

Formulation development of NGF requires condition be found for which the protein shows ≧1.5 years of chemical and physical stability at 2–8° C. We determined the approximate pH of maximal NGF stability by ascertaining NGF stability in succinate buffer at pH 4.2, 5.0, and 5.8, and acetate buffer at pH 5.0 and 5.8. NGF stability decreases above pH 6.0. The assays used to measure protein stability were IEC, SEC, RP-HPLC, SDS-PAGE, and the PC12 bioactivity assay. Formulation biocompatibility was determined by hemolysis testing.

Stability of NGF at 37° C.

Aggregation of NGF

The dimer/monomer equilibrium constant for murine NGF is smaller than 10–13 M at pH 4–7 (6, 7, 9, 12). NGF, therefore, assayed primarily as a dimer in the neutral pH SEC assay. A small amount of aggregated NGF (tetramer based on molecular weight standards) was observed in the control sample. This tetramer peak area increased with time at 37° C. A leading shoulder on this peak, indicating larger aggregates, was observed for all formulations after 38 days at 37° C. The time dependencies of aggregate formation for the various formulations are shown in FIG. 1. The succinate pH 5.8 formulation had the greatest aggregation rate. All other formulations had similar rates of aggregate formation. The addition of the surfactant Tween 20 offered no protection against aggregation in the pH 5.0 succinate formulation. During preparation, the NGF pH 5.8 succinate formulation had to be filtered through a 47 mm diameter 0.22 mm filter, whereas all other formulation were filterable through a 25 mm diameter filter. This is consistent with the high rate of aggregation observed at 37° C. in succinate buffer at pH 5.8.

Aggregation was also monitored using non-reduced SDS-PAGE (gels not shown). In the −70° C. control samples 3 bands were observed: monomer at 13.5 kDa, a very faint dimer band at approximately 26 kDa, and a slightly more intense band at 31 kDa. The 26 and 31 kDa bands became more intense on incubation at elevated temperatures. A small amount of large molecular weight aggregate (>97 kDa) was observed in all formulations after 38 days at 37° C. The intensity of this band was greatest in the pH 5.8 succinate formulation, consistent with the poor filterability and high aggregation rate observed by SEC for this formulation. Tween 20 prevented the formation of this high molecular weight aggregate at pH 5.0. With the exception of succinate at pH 5.8, these sizing methods do not differentiate between the quality of the NGF formulations.

NGF Monomer and Degradation Product Quantitation

Figure 2:
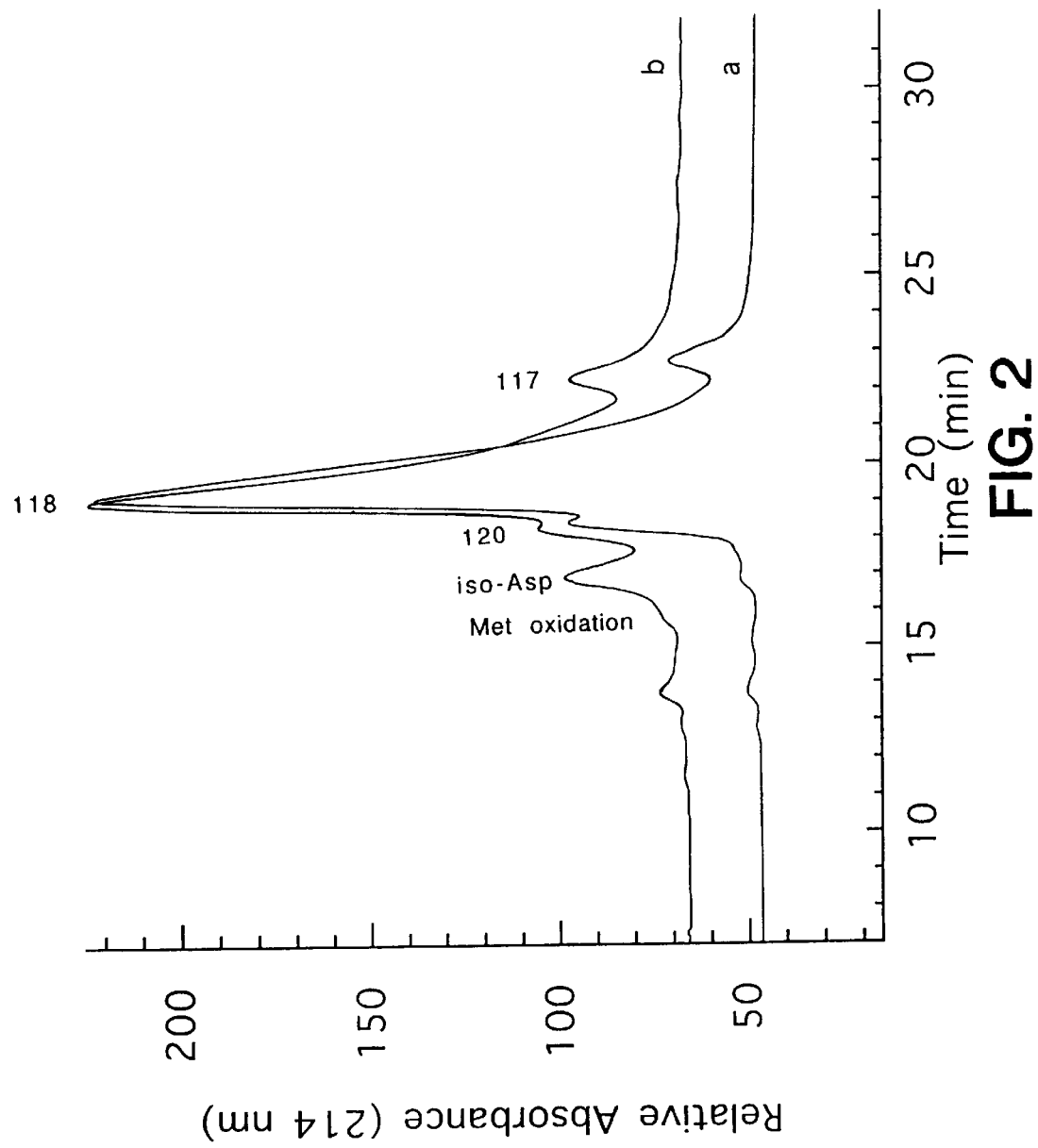
FIG. 2 depicts representative RP-HPLC chromatograms for NGF in succinate buffer at pH 5.0 (a) –70° C. control and (b) after 38 days of incubation at 37 degrees C.
Figure 3:
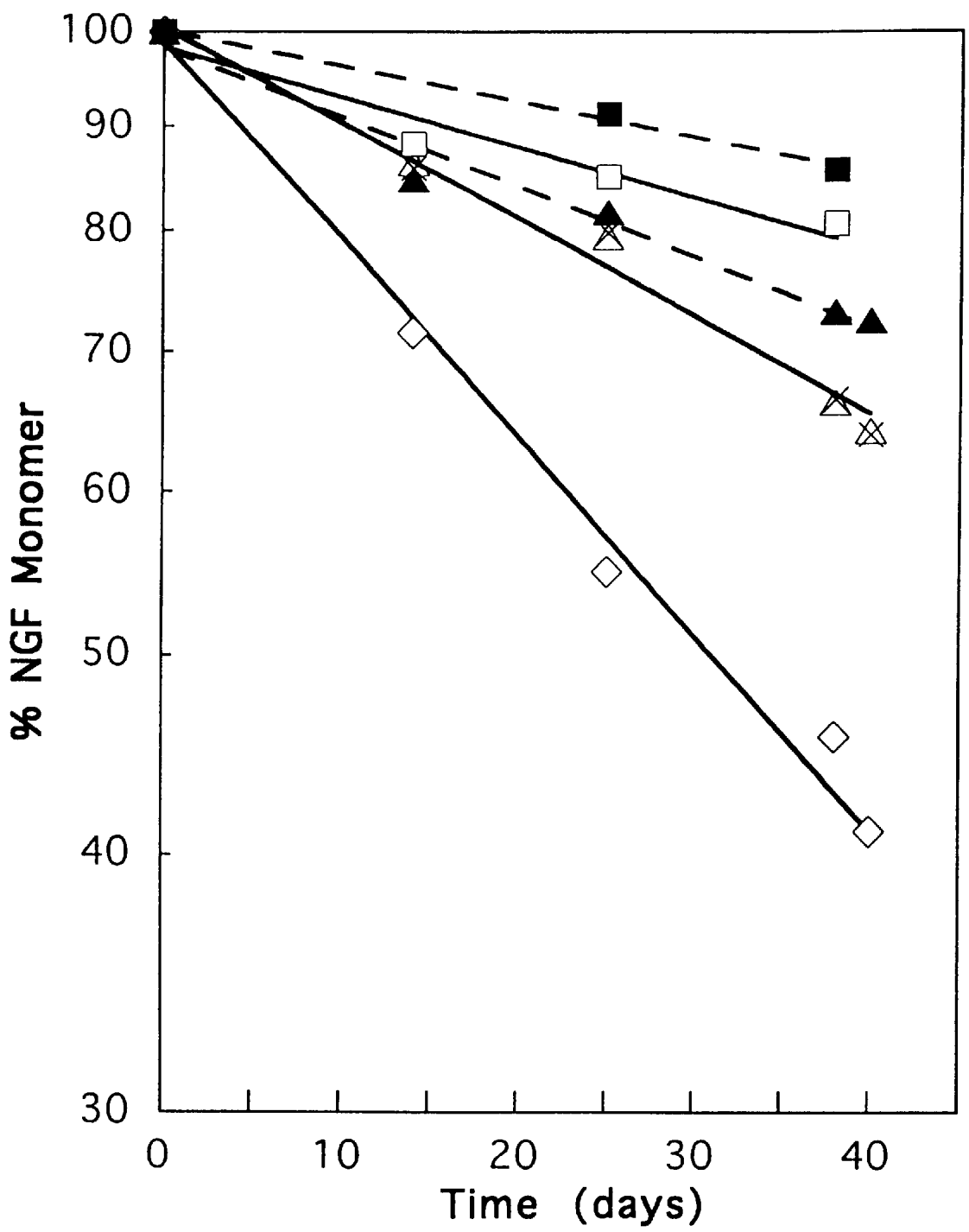
FIG. 3 depicts semilogarithmic plot of the percent NGF monomer remaining after incubation at 37° C. for various lengths of time as quantitated by RP-HPLC, (◇) succinate pH 4.2; (Δ) succinate pH 5.0; (□) succinate pH 5.8; (X) succinate pH 5.0 with 0.05% Tween 20; (▲) acetate pH 5.0; and (■) acetate pH 5.8. Curves are first order fits to the data.

The NGF used in these studies consisted of a 1:9:1 ratio of the three monomeric polypeptides containing 120, 118, and 117 amino acids. The 118 amino acid variant was produced by clipping of Ala120 and Arg119 from the C-terminus of the 120 parent; the 117 variant had an additional clip, Arg118 (8). At pH 5.0, the 117 variant has two fewer positive charges, and the 118 variant one fewer positive charge than the 120 parent. There is no significant difference in the bioactivity of the homodimers and heterodimers formed by the 117, 118, and 120 variants as measured by the PC12 and chick dorsal root ganglion assays (8). In the acidic, organic, RP mobile phase where NGF dissociates to monomer (8), the elution order is 120 before 118, then 117. Typical RP-HPLC chromatograms for NGF stored in pH 5.0 succinate buffer, for 38 days, at −70° C. and 37° C. are shown in FIG. 2. At elevated temperature, peak area is lost from the peaks defined as NGF (the sum of the 118 and 120 monomer peaks) with the iso-Asp, oxidized, and other NGF degradation peaks increasing in area. The 117 peak area was not included in the definition of NGF due to coelution of degradation products with this peak at elevated temperatures. The time dependence of NGF degradation at 37° C., and the apparent first order rate constants for this degradation, are shown in FIG. 3 and Table 1, respectively.

TABLE 1

Apparent First-Order Rate Constants for NGF Degradation at 37° C. as Determined by RP-HPLC.

| Buffer | pH | k (day-1) |
| --- | --- | --- |
| Succinate | 4.2 | 2.2 × 10 − 2 ± 1.0 × 10 − 3 |
|  | 5.0 | 1.1 × 10 − 2 ± 6.3 × 10 − 4 |
| (+Tween 20) | 5.0 | 1.1 × 10 − 2 ± 7.1 × 10 − 4 |
|  | 5.8 | 5.7 × 10 − 3 ± 9.7 × 10 − 4 |
| Acetate | 5.0 | 7.9 × 10 − 3 ± 8.0 × 10 − 4 |
|  | 5.8 | 4.0 × 10 − 3 ± 2.9 × 10 − 4 |

NGF stability decreased as the pH was lowered. In both the acetate and succinate pH 5.8 buffers NGF stability was greater than at pH 5.0. In succinate buffer at pH 4.2, the NGF degradation rate is further increased, with several hydrophobic degradation products being observed, possibly due to acid-induced cleavage at the Asp60-Pro61 linkage. Tween 20 had no affect on NGF stability in succinate buffer at pH 5.0 (FIG. 3). The acetate formulation appears to be somewhat better in maintaining NGF stability.

NGF Dimer Distribution

The three NGF monomers containing 117, 118, and 120 amino acids may combine to form the 117/117, 118/118 and 120/120 homodimers and the 117/118, 118/120, and 117/120 heterodimers. Association of these NGF variants has been shown to be random, with no monomer appearing to prefer any other (8, 9). The dynamic dissociation and reassociation of monomers to form various dimers (dimer exchange) is accelerated by low pH and increased temperature (9). For a random association process at equilibrium, and an initial 117/118/120 ratio of 1:9:1, the 118/118 homodimer will be the dominant dimer species with smaller amounts of the 117/118 and 118/120 dimers being formed.

The 118/118 and 117/120 dimers have the same effective net charge in the chosen IEC mobile phase and therefore coelute on IEC during NGF purification. This results in an initial non-equilibrium distribution of the monomer variants in NGF dimers in the NGF product. The 117/120 and 118/118 dimers dissociate giving the 117 and 120 monomers which will reassociate most frequently with 118 monomer to form 117/118 and 118/120 dimers. Due to the different charges on the monomers, the expected elution order of these dimers on cation-exchange chromatography is:

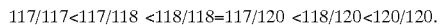

117/117<117/118 <118/118=117/120 <118/120<120/120.

Figure 4:
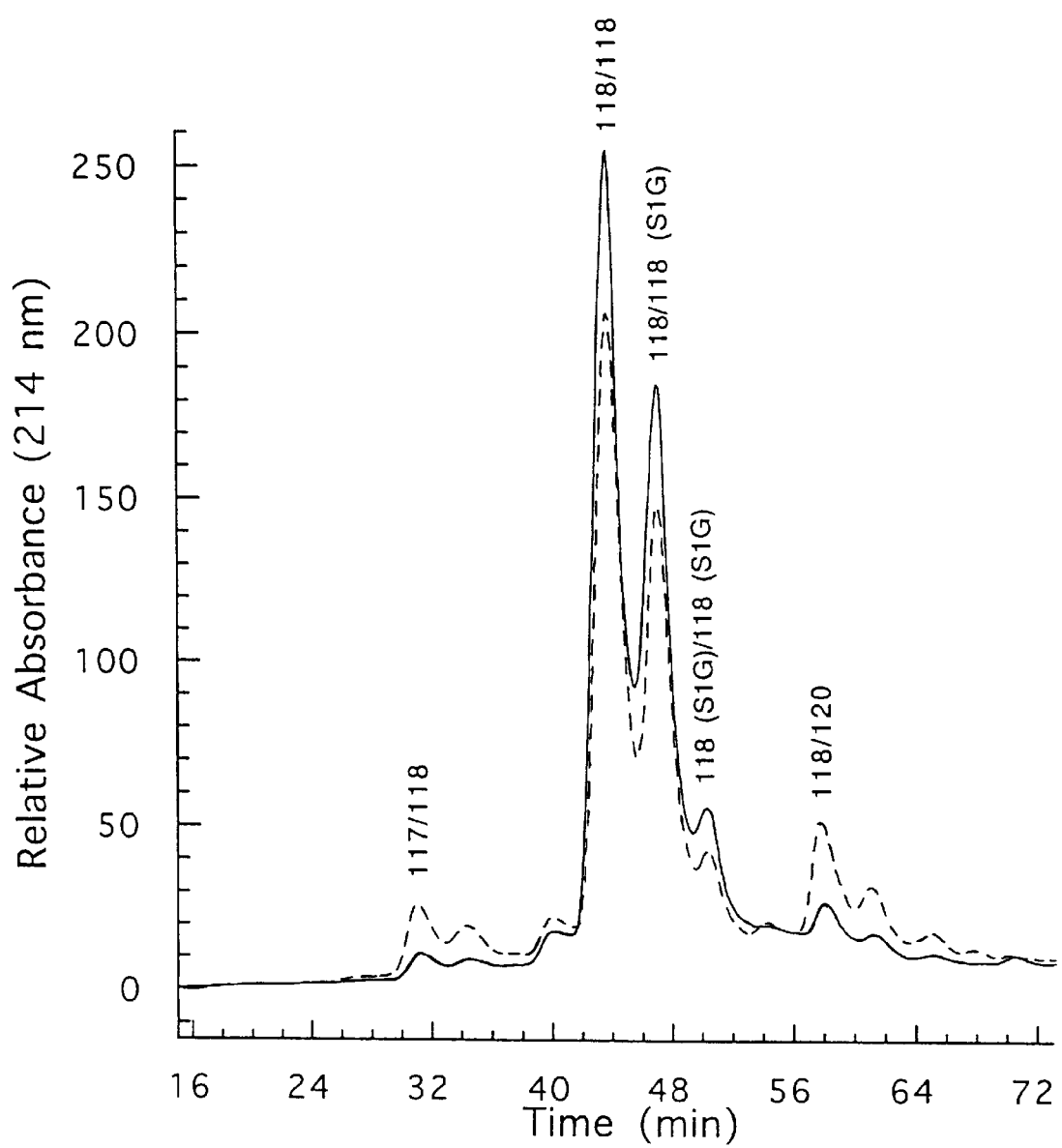
FIG. 4 depicts representative IEC chromatograms for NGF in acetate buffer at pH 5.0 after 38 days of incubation at (solid line) –70° C. and (dashed line) 37° C. Each dimer appears as a triplet in the chromatogram due to N-terminal Ser to Gly (S1G) conversion (13). The earliest peak in the triplet is the parent dimer, followed by a dimer with a single Ser to Gly conversion, and finally a dimer with a Ser to Gly conversion in both chains.

The most populated dimers are distinguishable by IEC (8) as shown in FIG. 4.

Figure 5:
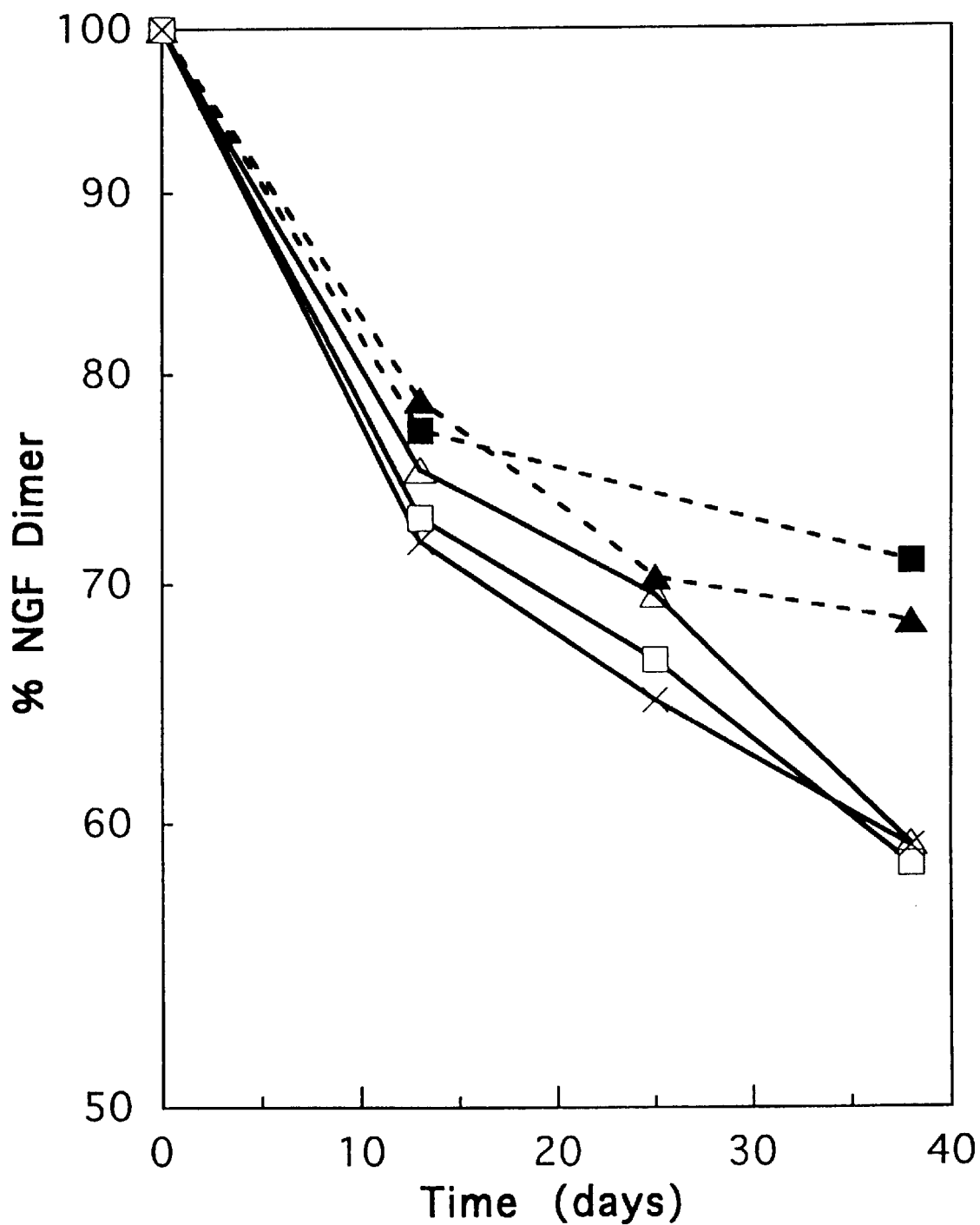
FIG. 5 depicts time dependence of the loss of NGF 118/118 and 117/120 dimers, by IEC, on incubation at 37° C., (Δ) succinate pH 5.0; (□) succinate pH 5.8; (X) succinate pH 5.0 with 0.05% Tween 20; (▲) acetate pH 5.0; and (■) acetate pH 5.8.

Representative IEC chromatograms for NGF at pH 5.0 in succinate buffer after 38 days at −70° C. and 37° C. are shown in FIG. 4. During NGF production, a fraction of the N-terminal serine residues are converted to glycine with no affect on NGF activity (13). NGF is quantitated here as the sum of the 118/118 homodimer and the 118/118 dimer with a Ser1 to Gly1 conversion in one of the two monomers (13) (and any coeluting 117/120 variants); the 117/118 and 118/120 peak areas are not included due to degradation products coeluting with these peaks. The rate of loss of NGF, as monitored by IEC at 37° C., is shown in FIG. 5. The degradation kinetics for the 118 dimer are multiphasic. The loss in main peak area before 13 days is largely due to rearrangement of the monomer variants between the possible dimer types. The data after 13 days more accurately describes NGF chemical degradation. NGF is most stable in the acetate formulations at pH 5.0 and 5.8, which have similar stability. NGF in succinate buffer at pH 5.8 and pH 5.0, with and without 0.05% Tween 20, all have similar stabilities. The hemolytic activity of each of the NGF formulations was also tested. None of the formulations showed significant red blood cell hemolysis (<0.1%). The bioactivity of NGF in each of the formulations was also determined, using the neurite extension PC12 assay. NGF was bioactive in all of the formulations after 38 days at 37° C. The large assay variability (approximately 50% error) did not allow quantitative bioactivity differences between these formulations to be determined.

Figure 6:
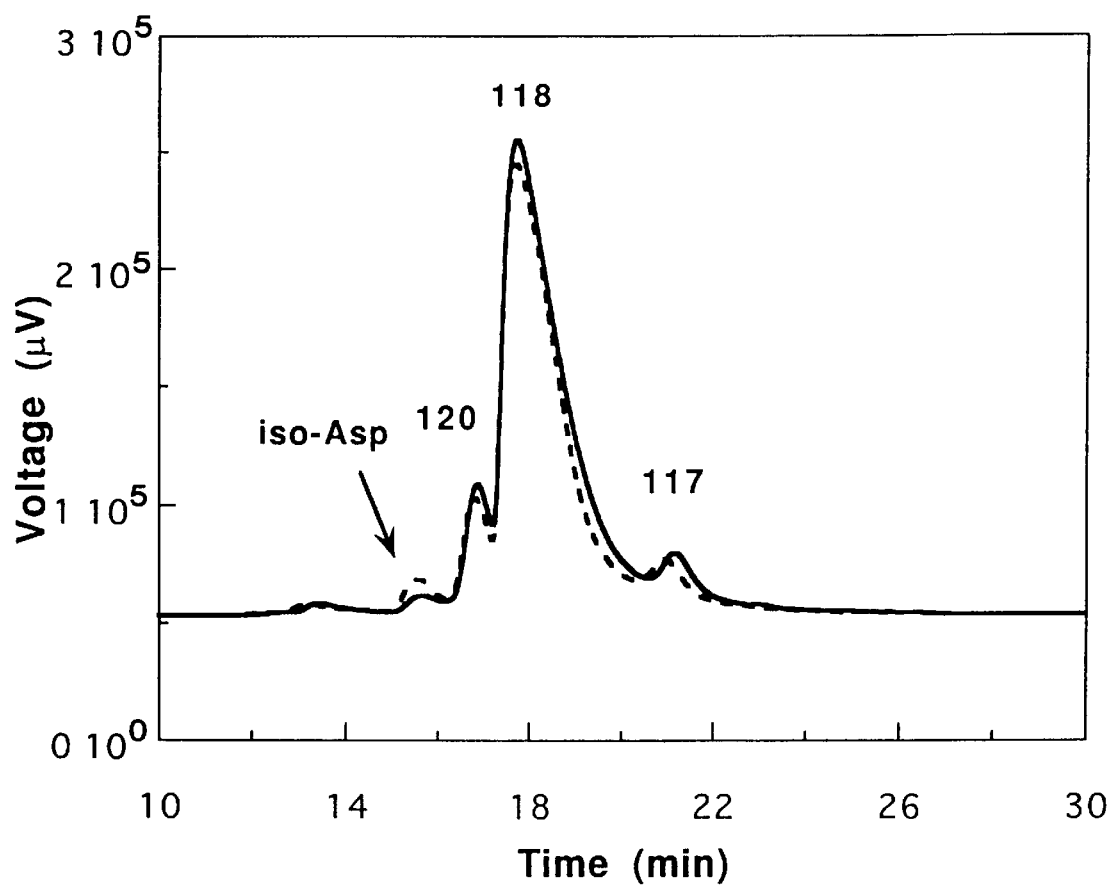
FIG. 6 depicts RP-HPLC chromatograms showing the stability of NGF after 1.6 years at (dashed line) 5° C. and (solid line) –70° C. The major degradation product at 5° C. is Asn93 to iso-Asp93 conversion.

A liquid formulation for NGF preferably has an adequate shelf-life at 5° C. The accelerated stability data at 37° C. showed NGF to be most stable in acetate buffer. Based on this data, NGF stability in the acetate pH 5.0 and 5.8 formulations was investigated for 1.6 years at 5° C. RP-HPLC chromatograms at pH 5.0 for the 1.6 year −70° C. control and 5° C. samples are shown in FIG. 6. The major degradation product was Asp-93 conversion to iso-Asp; smaller amounts of Met-37 and Met-92 oxidation were observed. The apparent first order rate constants for NGF degradation, quantitated by RP-HPLC, are 1.4×10−4±1.7× 10−5 d−1 and 6.8×10−5±7.0×10−6 d−1 at pH 5.0 and 5.8, respectively. At 5° C., IEC shows that NGF stability is approximately the same at pH 5.0 and 5.8, consistent with the 37° C. IEC data. Aggregation of the NGF dimers was not a significant degradation pathway at 5° C., only a 1% increase in aggregate was observed over 1.6 years of storage at 5° C.

Figure 7A:
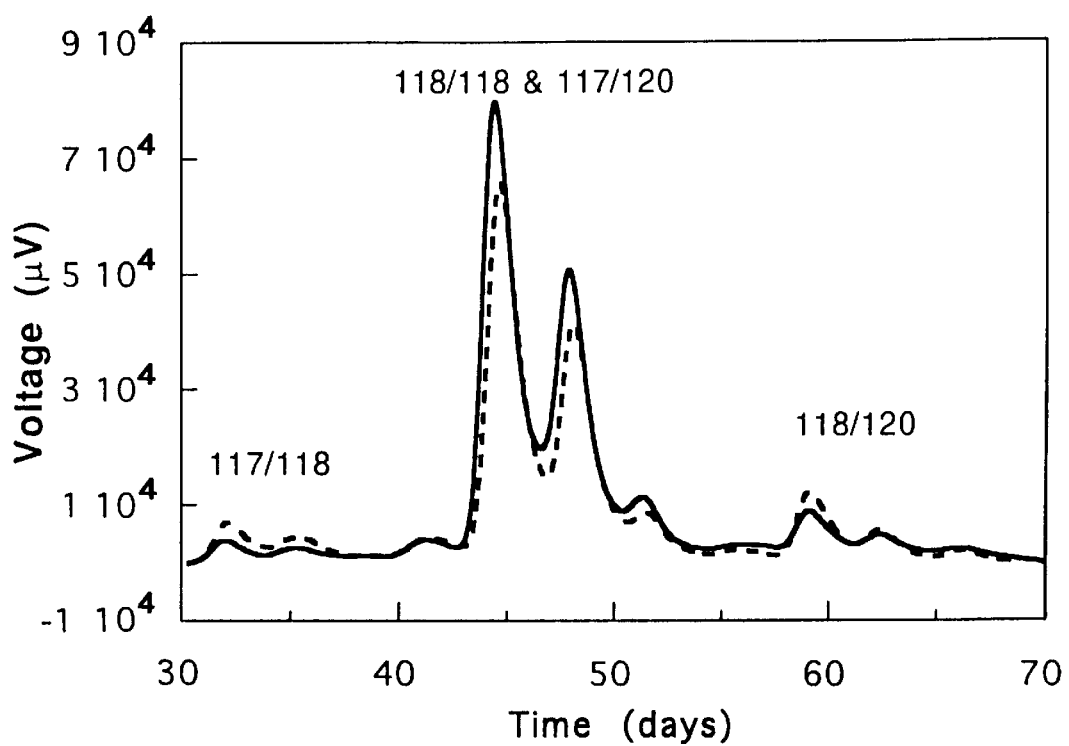
FIGS. 7A and 7B depict comparisons of NGF (solid line) –70° C. control and (dashed line) 5° C. IEC chromatograms after 1.6 years of incubation in acetate buffer at pH 5.0, (FIG. 7A) no acid treatment, and (FIG. 7B) acid treatment of samples prior to analysis.
Figure 7B:
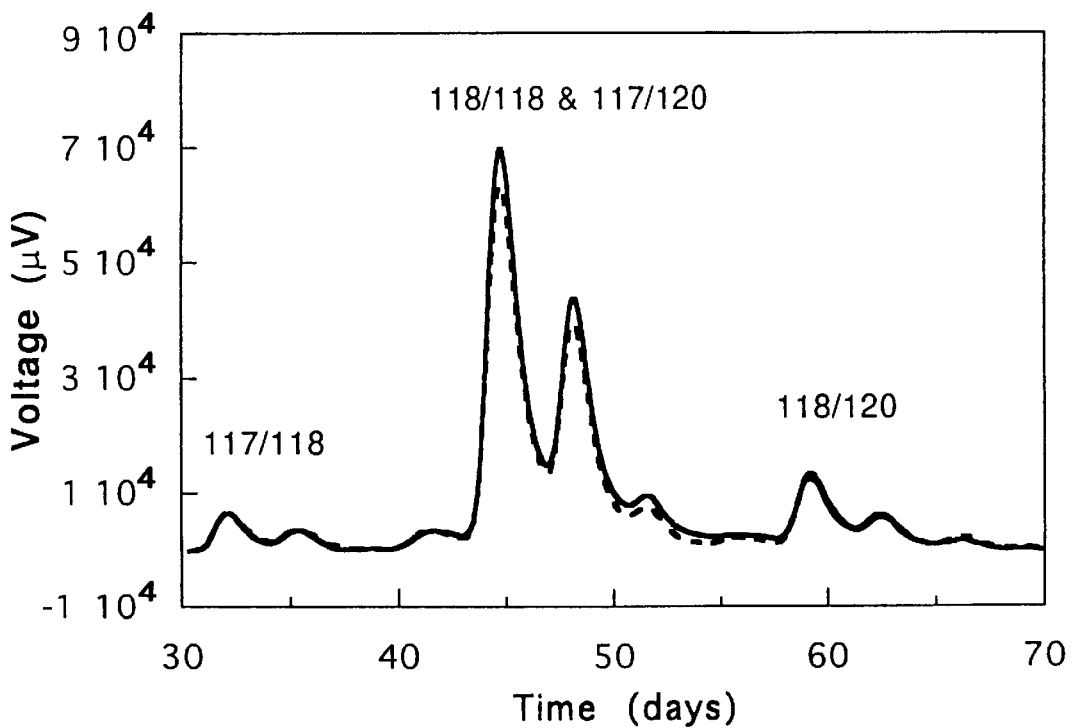

The interpretation of the IEC data at both 5° C. and 37° C., is complicated by dimer exchange, the exchange rate being slower at the lower temperature. To improve IEC quantitation, the dimer distribution was brought to equilibrium by incubation at pH 3.5 for 2 hours at 37° C. prior to IEC analysis (8,9,14). No new degradation products were observed after this treatment. The acetate pH 5.8 samples after 1.6 years of incubation at 5° C. are compared with controls before and after "acid treatment" in FIG. 7. The loss of main peak area to the peripheral peaks due to dimer exchange was eliminated by acid treatment, revealing the true degradation of NGF. Quantitation after acid treatment showed that 94 and 92% of the NGF main peaks remain after 1.6 years at 5° C. at pH 5.0 and pH 5.8, respectively, compared to 84 and 87% without acid treatment. For comparison, RP-HPLC analysis showed 93 and 96% of the NGF 118 and 120 monomers remaining at pH 5.0 and pH 5.8, respectively.

NGF chemical stability was shown to increase with pH, the pH of maximal stability being near pH 5.8. At a fixed pH, the RP-HPLC and IEC data at 5 and 37° C. were consistent in showing NGF chemical stability to be greater in acetate than succinate buffer. In addition, NGF aggregation was not a significant degradation pathway, except at pH 5.8 in succinate buffer. A complicating factor in the determination of NGF stability is that dimer exchange contributes to the apparent degradation of NGF dimers as determined by IEC. A more accurate representation of NGF chemical degradation can be obtained by pretreating the controls and samples with acid at 37° C. to bring the dimer distribution to equilibrium. Taken together, these data show that the optimal formulation and storage conditions for NGF stability are acetate butter at pH 5.8 with storage at 5° C.

Example II

Results from Phase II clinical trials indicate that patients with peripheral neuropathy disease require three dosings per week of rhNGF at either 0.3 or 0.1 μg/kg. This means that only 21 or 7 μg per dosing of rhNGF is needed for an average patient of body weight 70 kg. Using the current rhNGF liquid formulation (2 mg/mL in 10 mM sodium acetate, pH 5.5, 142 mM NaCl) and vial configuration (0.7 mL per vial) would have wasted a lot of drug product. Therefore, a new rhNGF formulation at low concentration, preferably multi-dose configuration, is required to reduce the cost and wastage of the product. The purpose of this study was to develop a stable multi-dose liquid formulation for rhNGF at 0.1 mg/mL with 1.8 mL fill in 3 cc glass vial for use in Phase III clinical trails. With this new configuration, each vial will give 180 μg protein and will provide at least 7 doses at the high dosing level (0.3 μg/kg) and 24 doses at the low dosing level (0.1 μg/mL).

In this study, the results on compatibility and stability of preservative containing 0.1 mg/ml rhNGF multi-dose liquid formulations at pH 5.5 are presented. A comparison between the stability of the new multi-dose liquid formulations at 0.1 mg/mL rhNGF and the current 2 mg/mL rhNGF formulation was also studied. Results on agitation, freezing and thawing, and light compatibility studies of the lead multi-dose liquid formulations for 0.1 mg/mL rhNGF were also reported.

In this study, rhNGF concentrated bulk formulated at 11.6 mg/mL in 10 mM sodium acetate, 142 mM sodium chloride at pH 5.5 with 20 mL filled in 100 cc glass vials was used. All chemical reagents and materials used in this Example are listed in Table 2.

TABLE 2

List of Materials rhNGF concentrated bulk, 11.6 mg/mL, in 10 mM sodium acetate, 142 mM sodium chloride, pH 5.5
Sodium acetate trihydrate, Genentech Release Materials Code G20136, Lot #S0766
Glacial acetic acid, Release Materials Code G20027-01, Lot S0567
Sodium Chloride, Release Materials Code G20136, Lot S1152
Benzyl alcohol, Release Materials Code G20226, Lot C0200
m-cresol, Sigma, Lot 107F-3497
Methylparaben, Napp Chemical Inc., Lot LM 86-6285
Propylparaben, Napp Chemical Inc., LL86-6241
Phenol, Release Materials Code G20136, Lot 620015, Lot B0901
Polysorbate 20, Release Materials Code G20091, Lot A1408
Pluronic acid (F68), Release Materials Code GXXXX, Lot XXXX
Sterile, pyrogen-free non-siliconized Type I clear glass 3 cc vials (Wheaton Tubing Products); prepared in Phase V per standard procedures
Sterile 13 mm Purcoat rubber stoppers, Clinical manufacturing, Genentech, Inc.
13 mm aluminum flip-off cap, Clinical manufacturing, Genentech, Inc.

Methods rhNGF Multi-dose Liquid Formulations Preparation rhNGF concentrated bulk was dialyzed into a formulation buffer consisting of 20 mM sodium acetate, 136 mM sodium chloride at pH 5.5 by ultrafiltration using Amicon Centriprep™ concentrator with molecular weight cutoff of 10,000 KD. This reformulated rhNGF bulk was then diluted to 0.15 mg/mL using the same formulation buffer for dialysis. Preservatives and surfactants used for compatibility screening and formulation development studies were added to this diluted rhNGF solution at their tested concentrations. Protein concentration for each formulation was then adjusted to 0.1 mg/mL by UV analysis using the appropriate formulation buffer. A list of preservatives and their concentrations used for physical compatibility with rhNGF in liquid formulations are given in Table 3.

TABLE 3

List of Preservative Screening Formulations for 0.1 mg/mL rhNGF

| Formulation buffer | Surfactant | Preservative |
|---|---|---|
| 20 mM acetate, pH 5.5<br>136 mM NaCl | none | 0.9% benzyl alcohol<br>0.25% phenol<br>0.45% phenol<br>0.25% m-cresol<br>0.18% methylparaben<br>0.02% propylparaben |
| 20 mM acetate, pH 5.5<br>136 mM NaCl | 0.01% Tween 20 | 0.9% benzyl alcohol<br>0.25% phenol<br>0.45% phenol<br>0.25% m-cresol<br>0.18% methylparaben<br>0.02% propylparaben |
| 20 mM acetate, pH 5.5<br>136 mM NaCl | 0.01% F68 | 0.9% benzyl alcohol<br>0.25% phenol<br>0.45% phenol<br>0.25% m-cresol |

TABLE 3-continued

List of Preservative Screening Formulations for 0.1 mg/mL rhNGF

| Formulation buffer | Surfactant | Preservative |
|---|---|---|
| | | 0.18% methylparaben<br>0.02% propylparaben |

Experimental Design

All rhNGF multi-dose liquid formulations prepared were sterile filtered through 0.22 μm filter prior to filling. Each formulations were aseptically filled into Type I, clear glass, 3 cc Wheaton vials with a fill volume of 1.8 mL. Vials were stoppered with 13 mm Purcoat stoppers and hand crimped with 13 mm aluminum flip-off caps.

For the preservative screening study, samples were stored at room temperature for 24 hours to determine physical compatibility. For the formulation development study, samples were stored at −70, 5, 25 and 40° C. At each timepoint, one sample/formulation/temperature was assayed.

Agitation studies were carried out at room temperature on the current 2 mg/mL rhNGF formulation, the multi-dose formulations that contain either 0.9% benzyl alcohol or 0.25% phenol in the absence of surfactant, and the 0.1 mg/mL rhNGF control that contains no surfactant and preservative. A 3 cc vial of each formulation tested was secured to a laboratory bench top shaker (Glas-Col) and agitated at 80 rpm for 6 and 24 hours. Samples collected after 6 and 24 hours of shaking were assayed by SE-HPLC, RP-HPLC, ELISA and RRA.

Freezing and thawing cycling was performed on the same formulations that used for agitation studies. One vial from each formulation tested was placed in −70° C. freezer and allowed to freeze for 24 hours. After 24 hours of freezing, samples were thawed at 5° C. for 24 hours. This freezing and thawing procedure was repeated up to 3 times. Samples collected at the end of the third cycle were assayed by SE-HPLC, RP-HPLC, ELISA and RRA.

The effect of light on stability of rhNGF was studied on the same formulations that used for agitation studies. One vial from each formulation was placed in a light box (Forma Scientific, Model 3890) under high intensity fluorescent light for 5 weeks. Control vials wrapped with aluminum foil were also placed in the light box. Light intensity was 20,000 lux which was about 15–20 times that of indoor fluorescent light, and the temperature of the light box was maintained at 28° C. Samples were assayed at 2 and 5 weeks by SEC-HPLC, ELISA and RRA.

Analytical Methodology

A. UV Analysis rhNGF concentration was determined by scanning from 240 to 360 nm using an HP 8452A UV-Vis spectrophotometer. Formulation buffer was used as a reference to blank the instrument, and the protein concentration in mg/mL was calculated from (A280−320)/1.5, where 1.5 is the extinction coefficient of rhNGF in mL/(mg.cm).

B. HPLC Analysis

The following HPLC methods were used.

| Reversed-Phase HPLC | |
|---|---|
| column: | YMC C4, 5 μm, 4.6 × 250 mm |
| mobile phase: | A: 0.05% (v/v) TFA, water |
| | B: 0.05% (v/v) TFA, 100% AcCN |
| gradient: | 25–27% B (26'), 27–50% B (4'), 50–80% B (1'), 80–25% B (4'), 25% B (20') |
| flow rate: | 1 mL/min |
| run time: | 55 min |
| temp: | 25° C. |
| LC: | HP-1090 |
| detection: | 214, 280 nm |
| injection: | 15 μg |

| Size Exclusion HPLC | |
|---|---|
| column: | Tosohaas TSK 2000SWXL, 5 μm, 7.8 × 300 mm |
| mobile phase: | 0.2M potassium phosphate, 0.45M KCl, pH 7.0 |
| gradient: | isocratic |
| flow rate: | 1.0 mL/min |
| run time: | 30 min |
| temp: | ambient |
| LC: | HP-1090 |
| detection | 214, 280 nm |
| injection: | 15 μg |

| Cation Exchange HPLC | |
|---|---|
| column: | Tosohaas TSK SP-5PW, 10 μm, 7.5 × 75 mm |
| mobile phase: | A: 10 mM sodium phosphate, 10% (v/v) AcCN, pH 7.0 |
| | B: A + 1M ammonium chloride |
| gradient: | 10–40% B (60'), 40–60% B (5'), 60–10% B (1'), 71–86% B (15') |
| flow rate: | 0.5 mL/min |
| run time: | 86 min |
| temp: | 35° C. |
| LC: | HP-1090 |
| detection | 214 nm |
| injection: | 15 μg |

C. ELISA

This assay with a range of 0.39–6.25 ng/mL was carried out by Immunoassay Services (Test Procedure Code SNGF:1 of Genentech, Inc.). Each rhNGF sample was diluted in assay diluent to two target concentrations of 5 and 2.5 ng/mL, and each dilution was submitted in micronic tubes in triplicate. The protein concentration in mg/mL was normalized to a $-70°$ C. internal reference standard which was submitted for the same assay.

D. Radioreceptor Assay (RRA)

This assay measures the ability of unlabeled rhNGF to compete with 125I-rhNGF for receptor binding on PC-12 cells. This assay was carried out by Bioassay Service (Genentech, Inc. Test Procedure SNGF:6) and has a range of 3–80 ng/mL. Each rhNGF sample was diluted in assay diluent to two target concentrations of 25 and 12.5 ng/mL, and each dilution was submitted in micronic tubes in duplicate. The protein concentration in mg/mL was normalized to a $-70°$ C. internal reference standard which was submitted for the same assay.

E. PC-12 Cell Survival Bioassay

This assay determines the ability of rhNGF to bind to its receptors and generate intracellular signals that result in the survival of PC-12 cells under serum-free culture conditions. This assay was carried out by Bioassay Service (Test Procedure SNGF:7) and has a range of 0.24–30 ng/mL. The active protein concentration in mg/mL was normalized to a $-70°$ C. internal reference standard which was submitted for the same assay.

F. Visual Inspection

Visual inspection was performed on all formulations in vials at the time of sampling. Samples were observed for solution clarity, color, opalescence and particulate formation.

G. pH Determination pH of all formulations was determined at each timepoint using a radiometer (model PHM82, Radiometer America Inc.) and a micro-electrode(model M1-410, Microelectrodes, Inc.). Standard solutions of pH 4.01 and pH 7.00 were used for the standardization and calibration of the radiometer prior to pH measurement.

H. Preservative Effectiveness Test

The lead rhNGF multi-dose liquid formulations which were stable at 5° C. for 6 months were sent to Northview Lab for bacterial challenge testing based on USP and EP standard criteria.

I. Circular Dichroism (CD) Analysis

An AVIV® spectropolarimeterModel 60 DS equipped with water bath and data processor was used to measure circular dichroism. Measurements were made at 20° C. Quartz cuvettes of 1.0 cm cell path length was used for measuring near-UV CD. The CD spectra was taken at 0.2 nm intervals, with a 0.5 nm bandwidth, and 3.0 second averaging time. Each sample for CD measurement was taken continuously for 24 hours. The CD data were expressed as the mean residue ellipticity [q], degree.cm2/decimole, using the mean residue weight of 120 for rhNGF.

Results

A preservative screening study was first performed to examine the physical compatibility of several commonly used preservatives with rhNGF at 0.1 mg/mL in the 20 mM sodium acetate formulation at pH 5.5. These preservatives include benzyl alcohol, phenol, m-cresol, methylparaben and propylparaben. In addition, the physical compatibility of these preservatives with rhNGF in the acetate formulation with the presence of surfactants such as polysorbate 20 and pluronic acid (F68) was also studied. The physical compatibility results are shown in Table 4.

TABLE 4

List of rhNGF Liquid Formulations Selected for Long Term Stability Testing

I. Current liquid formulation
   1. 2 mg/mL rhNGF in 10 mM acetate, 142 mM sodium chloride, pH 5.5

II. Control liquid formulations (no preservative)
   1. 0.1 mg/mL rhNGF in 20 mM acetate, 136 mM sodium chloride, pH 5.5
   2. 0.1 mg/mL rhNGF in 20 mM acetate, 136 mM sodium chloride, 0.01% F68, pH 5.5

III. Multi-dose liquid formulations
   1. 0.1 mg/mL rhNGF in 20 mM acetate, 136 mM sodium chloride, 0.9% benzyl alcohol, pH 5.5
   2. 0.1 mg/mL rhNGF in 20 mM acetate, 136 mM sodium chloride, 0.25% phenol, pH 5.5

TABLE 4-continued

List of rhNGF Liquid Formulations Selected for Long Term Stability Testing 3. 0.1 mg/mL rhNGF in 20 mM acetate, 136 mM sodium chloride, 0.01% F68, 0.9% benzyl alcohol, pH 5.5
4. 0.1 mg/mL rhNGF in 20 mM acetate, 136 mM sodium chloride, 0.01% F68, 0.25% phenol, pH 5.5

Among the preservatives used for screening, they are all physically compatible with rhNGF at 0.1 mg/mL in the acetate formulation at pH 5.5. In the presence of polysorbate 20 at 0.01% in the same formulation, only benzyl alcohol and phenol at final concentrations of 0.9% and 0.25% respectively were physically compatible with rhNGF. Phenol at 0.45% and m-cresol at 0.25% each formed a cloudy solution with rhNGF in the acetate formulation in the presence of polysorbate 20. The rhNGF solution also became slightly opalescent upon the addition of methylparaben at 0.18% or propylparaben at 0.02% to the polysorbate 20 containing acetate formulation. On the other hand, pluronic acid at 0.01% in the same formulation did not cause any physical incompatibility between rhNGF and all the preservatives tested.

Based on the preservative screening study results, several rhNGF multi-dose liquid formulations containing either 0.9% benzyl alcohol or 0.25% phenol in 20 mM acetate at pH 5.5 with and without 0.01% F68 were set up for long term stability study. A list of these formulations were given in Table 5.

TABLE 5

Physical Compatibility of Preservatives with 0.1 mg/mL rhNGF Liquid Formulations

| Formulation buffer | Surfactant | Preservative | Results |
|---|---|---|---|
| 20 mM acetate, pH 5.5 136 mM NaCl | none | 0.9% benzyl alcohol | co/cl |
| | | 0.25% phenol | co/cl |
| | | 0.45% phenol | co/cl |
| | | 0.25% m-cresol | co/cl |
| | | 0.18% methylparaben | co/cl |
| | | 0.02% propylparaben | co/cl |
| 20 mM acetate, pH 5.5 0.01% 136 mM NaCl | Tween 20 | 0.9% benzyl alcohol | co/cl |
| | | 0.25% phenol | co/cl |
| | | 0.45% phenol | cloudy |
| | | 0.25% m-cresol | cloudy |
| | | 0.18% methylparaben | sl. opal |
| | | 0.02% propylparaben | sl. opal |
| 20 mM acetate, pH 5.5 136 mM NaCl | 0.01% F68 | 0.9% benzyl alcohol | co/cl |
| | | 0.25% phenol | co/cl |
| | | 0.45% phenol | co/cl |
| | | 0.25% m-cresol | co/cl |
| | | 0.18% methylparaben | co/cl |
| | | 0.02% propylparaben | co/cl |

Stability of rhNGF in these formulations was assayed by the following techniques: SE-HPLC, RP-HPLC, IE-HPLC, ELISA, radioreceptor assay (RRA), PC-12 cell survival bioassay, pH, and visual inspection. The acceptability of a multi-dose liquid formulation for rhNGF will be based on comparison to the current liquid formulation which consists of 2 mg/mL rhNGF in 10 mM sodium acetate at pH 5.5, and 142 mM sodium chloride. In the other word, the preserved formulation should be as stable as the current liquid formulation. Results obtained to date represent 12 months at −70 and 5° C., 9 months at 25° C., and 3 months at 40° C. stability monitoring data.

Size-Exclusion Chromatography

Size-exclusion HPLC was employed to detect and quantitate aggregate formation in the rhNGF multi-dose liquid formulations as well as their control formulations which contain no preservative. Using this technique, rhNGF elutes as dimer (main peak) at a retention time of 8.6 minutes. Benzyl alcohol and phenol elute at 16 and 19 minutes respectively. The appearance of leading shoulder on the dimer main peak indicates the presence of aggregate of higher molecular weight. The data in Table 6 shows that rhNGF is stable to aggregate formation in all formulations containing 0.9% benzyl alcohol as preservative.

TABLE 6

Effect of preservative on aggregation of 0.1 mg/mL rhNGF in liquid formulations was determined by SEC-HPLC. Samples were stored at 5° C. for 12 months, 25° C. for 9 months and 40° C. for 3 months.

| Formulation buffer | Surfactant | Preservative | % Aggregate 5° C. | 25° C. | 40° C. |
|---|---|---|---|---|---|
| 10 mM acetate, pH 5.5 145 mM NaCl, 2 mg/mL | none | none | 0 | 0.2 | 0.4 |
| 20 mM acetate, pH 5.5 136 mM NaCl, 0.1 mg/mL | none | none | 0 | 0 | 0 |
| 20 mM acetate, pH 5.5 136 mM NaCl, 0.1 mg/mL | none | 0.9% benzyl. alc. | 0 | 0 | 0 |
| 20 mM acetate, pH 5.5 136 mM NaCl, 0.1 mg/mL | none | 0.25% phenol | 0 | 0.4 | 0.5 |
| 20 mM acetate, pH 5.5 136 mM NaCl, 0.1 mg/mL | 0.01% F68 | none | 0 | 0 | 0 |
| 20 mM acetate, pH 5.5 136 mM NaCl, 0.1 mg/mL | 0.01% F68 | 0.9% benzyl alc. | 0 | 0 | 0 |
| 20 mM acetate, pH 5.5 136 mM NaCl, 0.1 mg/mL | 0.01% F68 | 0.25% phenol | 0 | 0.5 | 0.5 |

A small amount of aggregate (less than 1%) was detected in the phenol containing formulations (with and without 0.01% F68 as surfactant) after 3 months at 40° C. and 9 months at 5° C. Total protein recovery of these samples, compared to their −70° C. controls, was given in Table 7.

TABLE 7

Quantitation of total rhNGF by SE-HPLC. Samples were stored at 5° C. for 12 months, 25° C. for 9 months and 40° C. for 3 months.

| Formulation buffer | Surfactant | Preservative | % Recovery 5° C. | 25° C. | 40° C. |
|---|---|---|---|---|---|
| 10 mM acetate, pH 5.5 145 mM NaCl, 2 mg/mL | none | none | 102 | 102 | 102 |
| 20 mM acetate, pH 5.5 136 mM NaCl, 0.1 mg/mL | none | none | 101 | 101 | 101 |
| 20 mM acetate, pH 5.5 136 mM NaCl, 0.1 mg/mL | none | 0.9% benzyl alc. | 102 | 99 | 101 |
| 20 mM acetate, | none | 0.25% phenol | 99 | 97 | 98 |

TABLE 7-continued

Quantitation of total rhNGF by SE-HPLC. Samples were stored at 5° C. for 12 months, 25° C. for 9 months and 40° C. for 3 months.

| Formulation | | | % Recovery | | |
|---|---|---|---|---|---|
| buffer | Surfactant | Preservative | 5° C. | 25° C. | 40° C. |
| pH 5.5 136 mM NaCl, 0.1 mg/mL 20 mM acetate, pH 5.5 | 0.01% F68 | none | 101 | 101 | 98 |
| 136 mM NaCl, 0.1 mg/mL 20 mM acetate, pH 5.5 | 0.01% F68 | 0.9% benzyl alc. | 101 | 99 | 99 |
| 136 mM NaCl, 0.1 mg/mL 20 mM acetate, pH 5.5 136 mM NaCl, 0.1 mg/mL | 0.01% F68 | 0.25% phenol | 100 | 97 | 97 |

Current formulation, controls and benzyl alcohol containing formulations had 99% or greater protein recovery after 9 months at 25° C., while phenol containing formulations had 97% for the same storage time and temperature. These results indicate that rhNGF is more compatible and stable with benzyl alcohol than phenol in all formulations studied.

Reversed-Phase HPLC

Figure 8:
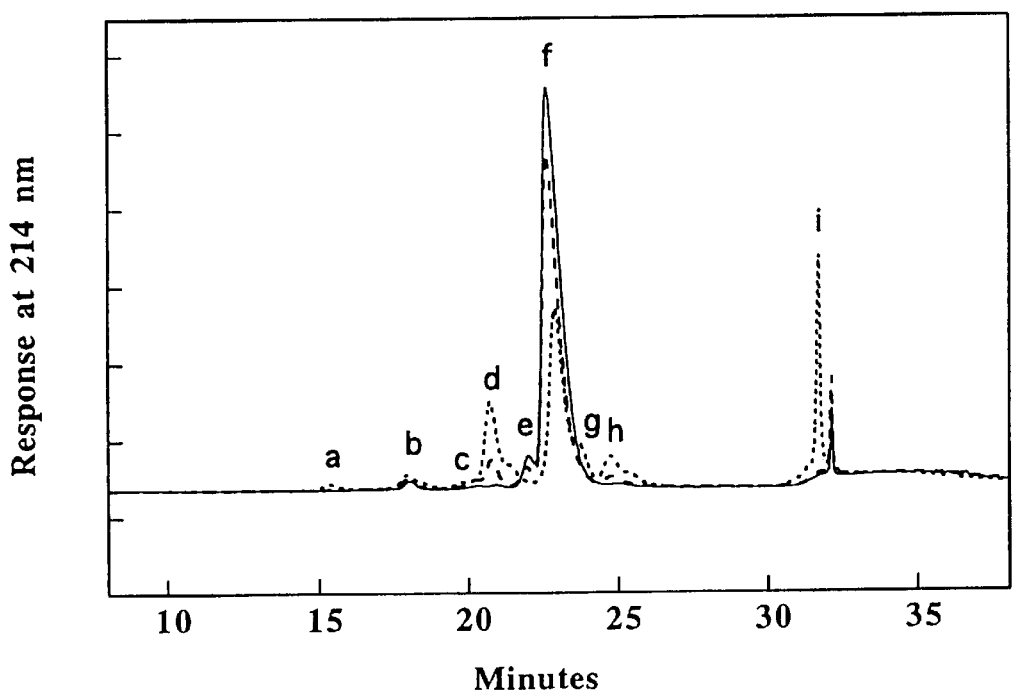
FIG. 8 depicts RP-HPLC chromatograms of 0.1 mg/ml rhNGF in 10 mM acetate at pH 5.5 and 142 mM NaCl stored at 5° C. (solid line), 25° C. (dashed line), and 40° C. (dotted line) for 3 months. Peak (a) contains di-oxidized rhNGF; peak (b) contains deamidated rhNGF; peak (c) contains mono-oxidized rhNGF; peak (d) contains Iso-aspartate; peak (e) contains 120 rhNGF; peak (f) contains 118 rhNGF; peak (g) contains N-terminally clipped rhNGF; peak (h) contains misfolded rhNGF; and peak (i) contains protein eluted at gradient ramp.

The rhNGF used in this study consists of mainly 118/118 homodimer and a small amount of 120/120 homodimer. Under the conditions of reversed-phase chromatography, the two rhNGF dimeric forms are dissociated and their monomers are separated. RP-HPLC separates the rhNGF monomers based on the hydrophobicity of each species. The 118 monomer which is more hydrophobic than the 120 monomer elutes at a retention time of 23 minutes. The 120 monomer elutes as a small peak in front of the 118 monomer peak. Comparison of RP-HPLC chromatograms of rhNGF in the benzyl alcohol preserved formulation containing no surfactant at 5, 25, and 40° C. are shown in FIG. 8. The degradation of rhNGF stored at elevated temperatures was mainly due to the formation of iso-aspartate, loss in 118 and 120 monomer peak areas, clip formation and increase in misfolded rhNGF as determined by RP-HPLC. The mono- and di-oxidized rhNGF peaks and the deamidated rhNGF peak remain unchanged. In this study, rhNGF is defined as the sum of the 118 and 120 monomer peak areas by RP-HPLC, and the results are reported as percent rhNGF remaining as compared to the −70° C. controls.

Figure 9:
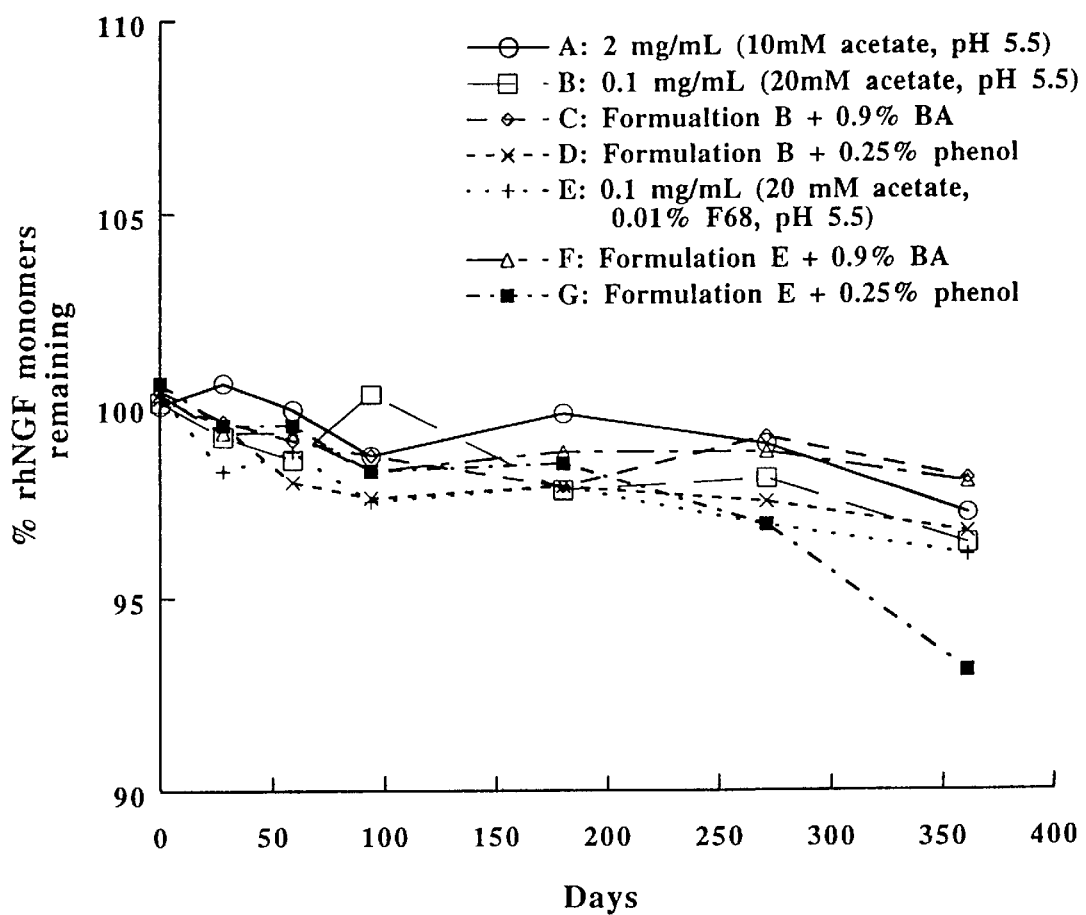
FIG. 9 depicts determination of rhNGF monomers (118 and 120) remaining in rhNGF formulations after 12 months at 5 degrees C. by reversed-phase HPLC. Formulation A (-⊖-) contains 2 mg/ml rhNGF (142 mM NaCl, 10 mM acetate, pH 5.5); formulation B (-□-) contains 0.1 mg/mL rhNGF (136 mM NaCl, 20 mM acetate, pH 5.5); formulation C (--◇--) contains formulation B plus 0.9% BA; formulation D (--x--) contains formulation B plus 0.25% phenol; formulation E (---+---) contains 0.1 mg/mL rhNGF (136 mM NaCl, 20 mM acetate, 0.01%F68, pH 5.5); formulation F (—Δ--) contains formulation E plus 0.9% BA; and formulation G (--■--) contains formulation E plus 0.25% phenol.
Figure 10:
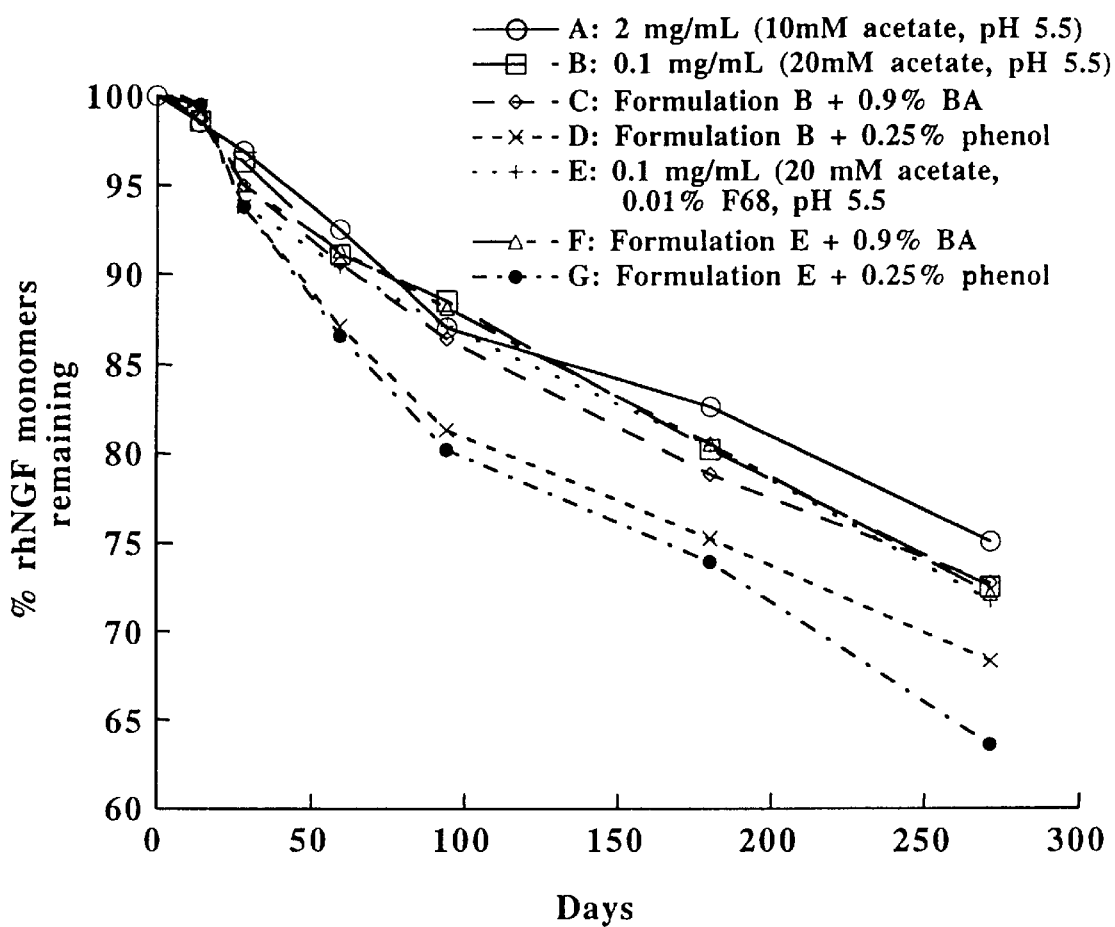
FIG. 10 depicts determination of rhNGF monomers (118 and 120) remaining in rhNGF formulations after 9 months at 25 degrees C. by reversed-phase HPLC. Formulation A (-★-) contains 2 mg/ml (10 mM acetate, pH 5.5); formulation B (-□-) contains 0.1 mg/ml (20 mM acetate, pH 5.5); formulation C (--◇--) contains formulation B plus 0.9% BA; formulation D (--x--) contains formulation B plus 0.25% phenol; formulation E (--+--) contains 0.1 mg/mL (20 mM acetate, 0.01% F68, pH5.5); formulation F (-Δ--) contains formulation E plus 0.9% BA; and formulation G (--●--) contains formulation E plus 0.25% phenol.

Decrease in percent protein remaining due to the loss of 118 and 120 monomer peak areas assayed by RP-HPLC is the major degradation for rhNGF in liquid formulation. At 5° C., the stability of rhNGF in multi-dose formulations as determined by RP-HPLC are essentially equivalent to the non-preserved control formulations as well as the current formulation (more than 95% rhNGF remaining after 12 months) except for the phenol preserved formulation containing 0.01% F68 (FIG. 9). This formulation had slightly less percent rhNGF remaining (93%) after 12 months at 5° C. At 25° C., rhNGF is obviously less stable in the presence of 0.25% phenol than 0.9% benzyl alcohol as preservative in the 20 mM acetate formulation at pH 5.5 (FIG. 10). The combination of phenol and F68 in the acetate formulation caused more degradation of the protein than the presence of phenol alone.

Figure 11:
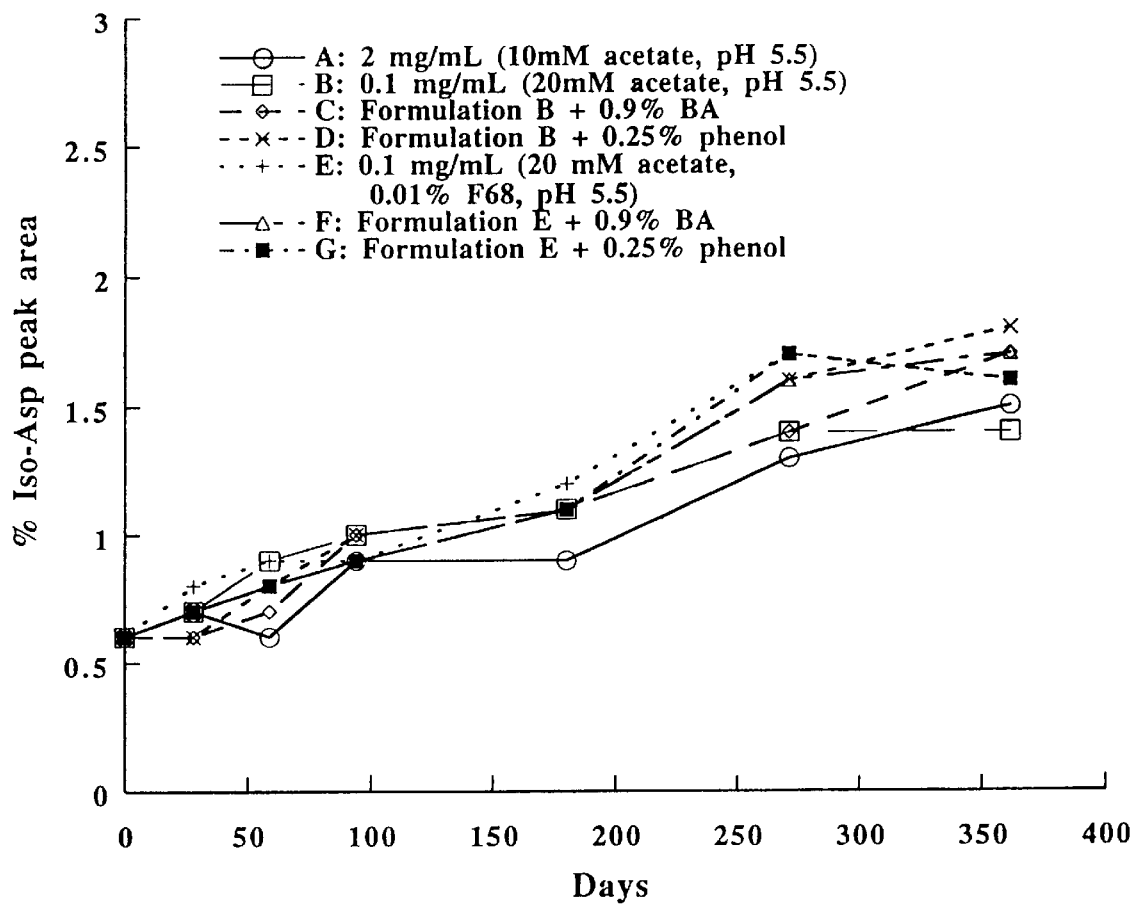
FIG. 11 depicts effect of preservative on Iso-aspartate formation of rhNGF in liquid multi-dose formulations stored at 5 degrees C. for 12 months as determined by RP-HPLC. Formulation A (-⊖-) contains 2 mg/mL (10 mM acetate, pH 5.5); formulation B (-□-) contains 0.1 mg/mL (20 mM acetate, pH 5.5); formulation C (--◇--) contains formulation B plus 0.9% BA; formulation D (--x--) contains formulation B plus 0.25% phenol; formulation E (--+--) contains 0.1 mg/mL (20 mM acetate, 0.01% F68, pH 5.5); formulation F (—Δ--) contains formulation E plus 0.9% BA; and formulation G (--■--) contains formulation E plus 0.25% phenol.
Figure 12:
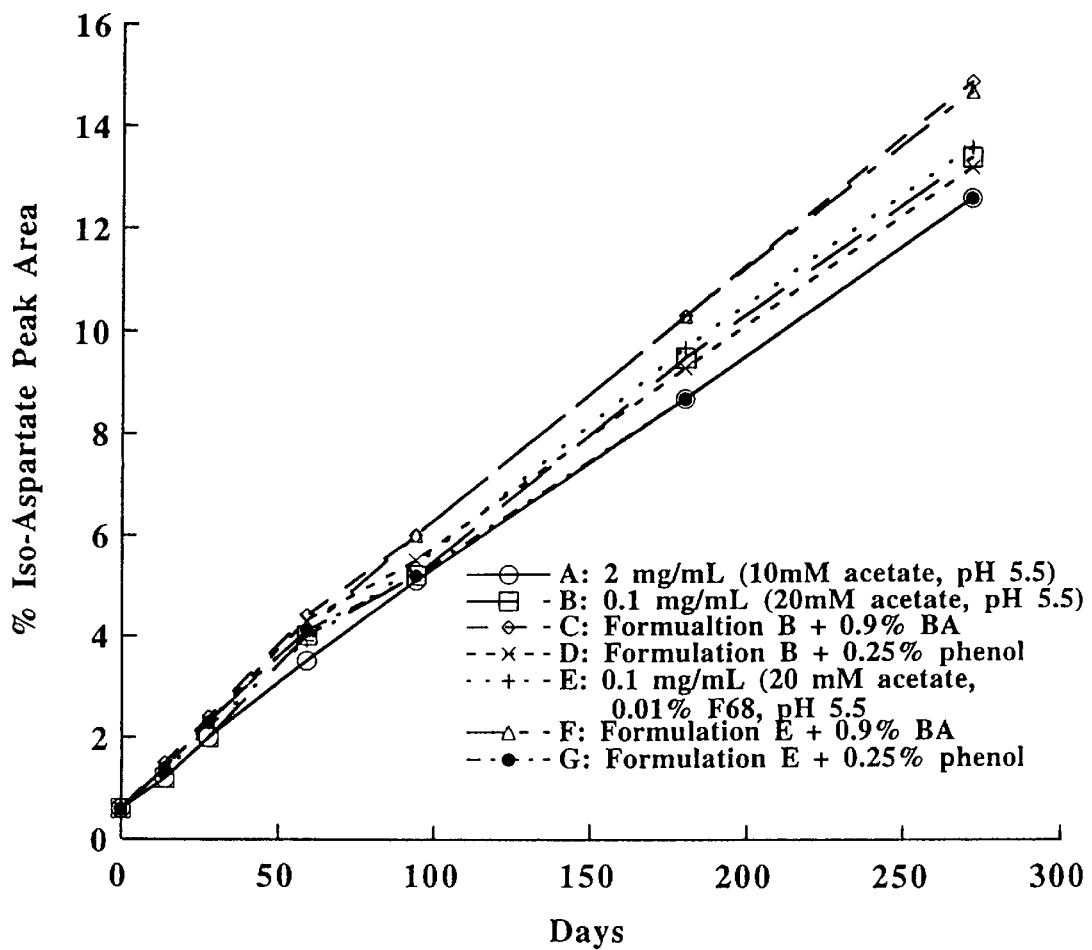
FIG. 12 depicts effect of preservative on Iso-aspartate formation of rhNGF in liquid multi-dose formulations stored at 25 degrees C. for 9 months as determined by RP-HPLC. Formulation A (-⊖-) contains 2 mg/mL (10 mM acetate, pH 5.5); formulation B (-□-) contains 0.1 mg/mL (20 mM acetate, pH 5.5); formulation C (--◇--) contains formulation B plus 0.9% BA; formulation D (--x--) contains formulation B plus 0.25% phenol; formulation E (--+--) contains 0.1 mg/mL (20 mM acetate, 0.01% F68, pH 5.5); formulation F (-Δ--) contains formulation E plus 0.9% BA; and formulation G (--■--) contains formulation E plus 0.25% phenol.

Iso-aspartate formation of rhNGF in liquid form is time and temperature dependent. The rate of iso-aspartate formation increases with increase in time and temperature. At 5° C., all formulations show a similar rate of iso-aspartate formation (FIG. 11). There was about 1.5% iso-aspartate formed in all rhNGF multi-dose formulations and their non-preserved control formulations after 12 months at 5° C. However, the rate of iso-aspartate formation is slightly higher in the rhNGF formulations preserved with 0.9% benzyl alcohol than the control formulations and phenol preserved formulations stored at 25° C. (FIG. 12). Since iso-aspartate formation of rhNGF does not affect the bioactivity of the protein, the effect of preservative on iso-aspartate formation of rhNGF is not a major concern.

Cation Exchange Chromatography

Figure 13:
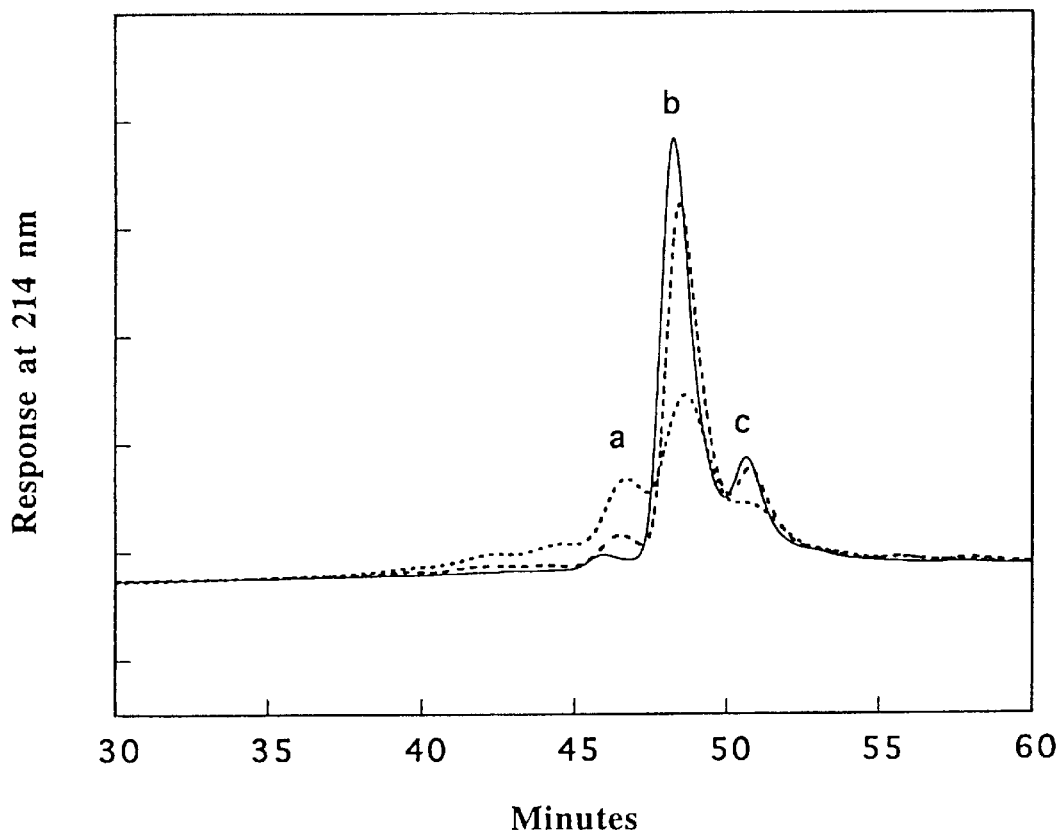
FIG. 13 depicts cation exchange HPLC chromatograms of 0.1 mg/ml rhNGF in 10 mM acetate at pH 5.5 and 142 mM NaCl stored at 5 degrees C. (solid line), 25 degrees C. (dashed line), and 40 degrees C. (dotted line) for 3 months. Peak (a) contains mono and di-oxidized 118/118 and oxidized N-terminally clipped rhNGF; peak (b) contains 118/118 rhNGF homodimer; and peak (c) contains Ser-Gly 118/118 rhNGF (1-chain).

IE-HPLC chromatograms for rhNGF in the current formulation at 3 months at 5, 25, and 40° C. are shown in FIG. 13. There are three major peaks observed. The predominant peak is the 118/118 dimer (peak b) which elutes at about 48 minutes. The peak c behind the main peak is from a serine to glycine substitution at position 1 in one of the two dimer chain. The peak a in front of the main peak is believed to be the oxidized 118/118 and oxidized N-terminally clipped rhNGF. At elevated temperatures (25 and 40° C.), degradation of rhNGF as determined by IE-HPLC is characterized by the decrease in peak areas of the 118/118 main peak and the serine to glycine substituted 118/118 dimer and the increase in peak a area. In this study, rhNGF is defined as the sum of the 118/118 dimer (peak b) and one chain serine to glycine dimer (peak c) peak areas by IE-HPLC, and the results are reported as percent rhNGF remaining as compared to the −70° C. controls.

Figure 14:
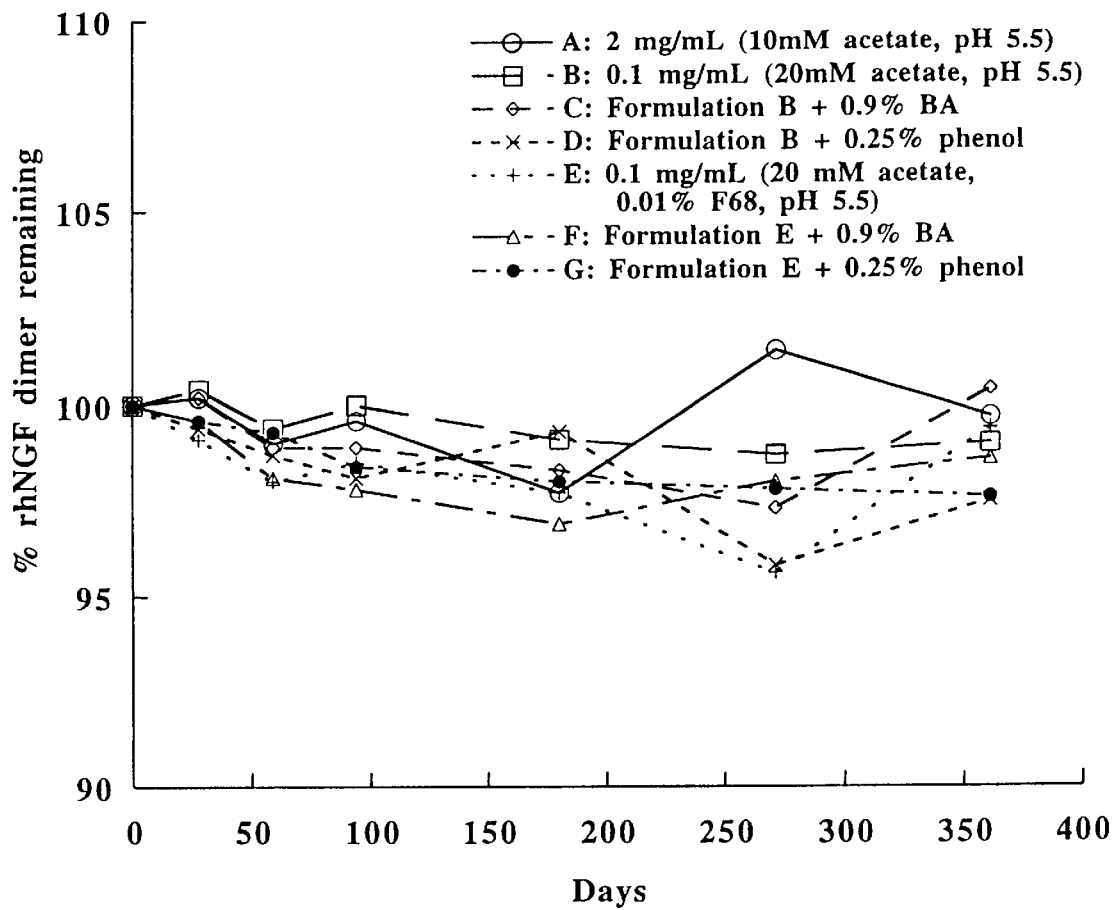
FIG. 14 depicts determination of rhNGF dimer (118/118) remaining in rhNGF formulations after 12 months at 5 degrees C. by cation exchange HPLC. Formulation A (-⊖-) contains 2 mg/mL (10 mM acetate, pH 5.5); formulation B (-□-) contains 0.1 mg/mL (20 mM acetate, pH 5.5); formulation C (--◇--) contains formulation B plus 0.9% BA; formulation D (--x--) contains formulation B plus 0.25% phenol; formulation E (--+--) contains 0.1 mg/mL (20 mM acetate, 0.01% F68, pH 5.5); formulation F (-Δ--) contains formulation E plus 0.9% BA; and formulation G (--●--) contains formulation E plus 0.25% phenol.
Figure 15:
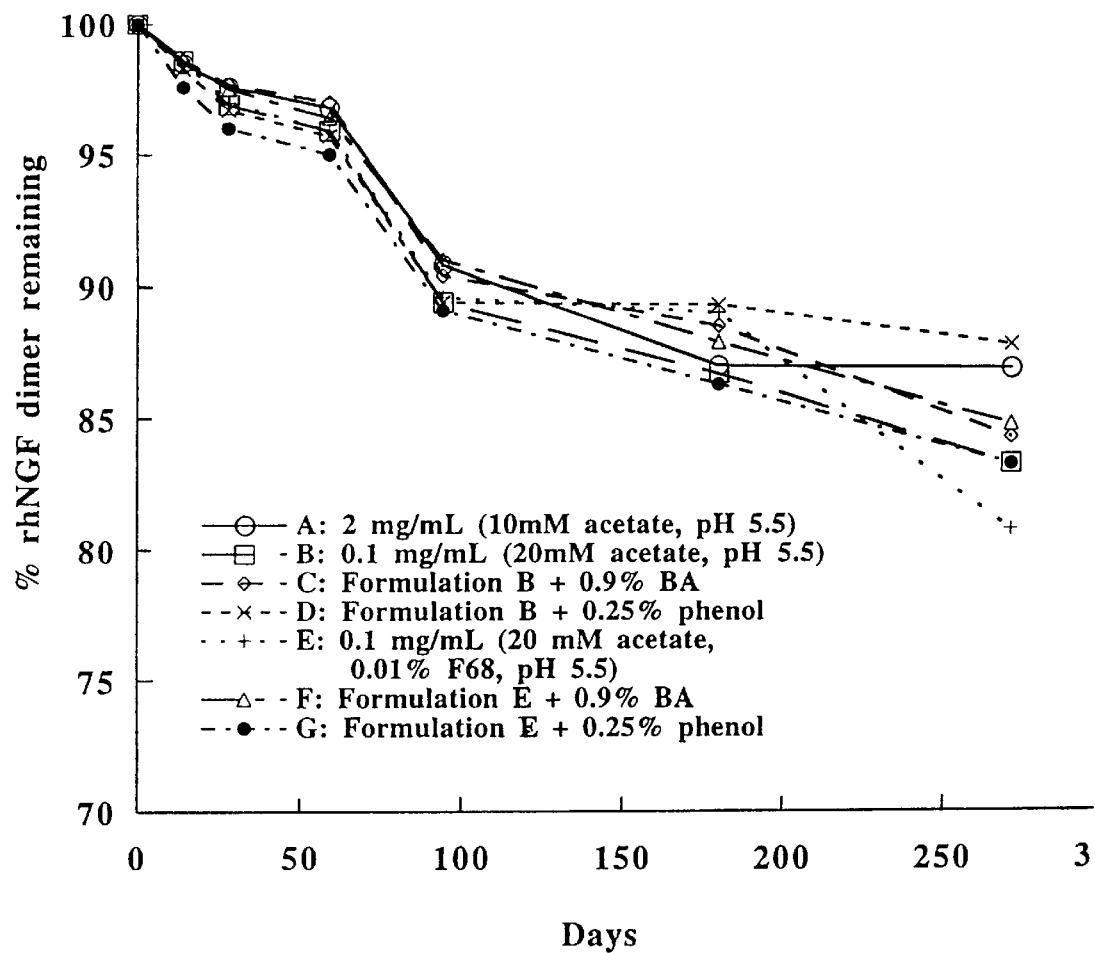
FIG. 15 depicts determination of rhNGF dimer (118/118) remaining in rhNGF formulations after 9 months at 25 degrees C. by cation exchange HPLC. Formulation A (-0-) contains 2 mg/mL (10 mM acetate, pH 5.5); formulation B (-□-) contains 0.1 mg/mL (20 mM acetate, pH 5.5); formulation C (--◇--) contains formulation B plus 0.9% BA; formulation D (--x--) contains formulation B plus 0.25% phenol; formulation E (--+--) contains 0.1 mg/mL (20 mM acetate, 0.01% F68, pH 5.5); formulation F (-Δ--) contains formulation E plus 0.9% BA; and formulation G (--●--) contains formulation E plus 0.25% phenol.

FIGS. 14 and 15 show the percent rhNGF remaining in all rhNGF formulations by IE-HPLC after 12 months at 5° C. and 9 months at 25° C., respectively. At 5° C., the peak area of peaks b and c for all rhNGF formulations remained unchange after 12 months. At 25° C., all rhNGF formulations show a similar rate of degradation, and there was no significant difference in stability between the multi-dose formulations and the control formulations as assessed by IE-HPLC.

ELISA

The data in Table 8 show the percent rhNGF remaining at 5, 25 and 40° C. after 12, 9 and 3 months of storage, respectively.

TABLE 8

Stability of current and selected multi-dose liquid formulations for rhNGF determined by ELISA after 12 months at 5° C., 9 months at 25° C., and 3 months at 40° C.

| Formulation | | | % rhNGF [a]Remaining | | |
|---|---|---|---|---|---|
| buffer | Surfactant | Preservative | 5° C. | 25° C. | 40° C. |
| 10 mM acetate, pH 5.5 145 mM NaCl, 2 mg/mL | none | none | 101.2 | 89.1 | 102.2 |
| 20 mM acetate, pH 5.5 136 mM NaCl, 0.1 mg/mL | none | none | 97.8 | 102.0 | 94.4 |
| 20 mM acetate, pH 5.5 136 mM NaCl, 0.1 mg/mL | none | 0.9% benzyl alc. | 103.1 | 92.9 | 97.1 |
| 20 mM acetate, pH 5.5 136 mM NaCl, 0.1 mg/mL | none | 0.25% phenol | 111.3 | 88.5 | 91.6 |
| 20 mM acetate, | 0.01% F68 | none | 98.5 | 102.7 | 92.7 |

TABLE 8-continued

Stability of current and selected multi-dose liquid formulations for rhNGF determined by ELISA after 12 months at 5° C., 9 months at 25° C., and 3 months at 40° C.

| Formulation buffer | Surfactant | Preservative | % rhNGF [a]Remaining 5° C. | 25° C. | 40° C. |
|---|---|---|---|---|---|
| pH 5.5 136 mM NaCl, 0.1 mg/mL | | | | | |
| 20 mM acetate, pH 5.5 136 mM NaCl, 0.1 mg/mL | 0.01% F68 | 0.9% benzyl alc. | 101.9 | 92.6 | 87.7 |
| 20 mM acetate, pH 5.5 136 mM NaCl, 0.1 mg/mL | 0.01% F68 | 0.25% phenol | 103.4 | 92.5 | 82.6 |

[a]Calculated as a percentage of assay response for −70° C. control sample at the same storage period.

Results were normalized to the −70° C. controls stored at the same temperature for the same period of time. There were no significant difference between the benzyl alcohol and phenol preserved formulation either in the presence or absence of 0.01% F68 as surfactant for all temperatures and time points studied.

Radioreceptor Binding Activity (RRA)

The RRA results are presented in Table 9 and are normalized to the −70° C. controls.

TABLE 9

Stability of current and selected multi-dose liquid formulations for rhNGF determined by RRA after 12 months at 5° C., 9 months at 25° C., and 3 months at 40° C.

| Formulation buffer | Surfactant | Preservative | % rhNGF [a]Remaining 5° C. | 25° C. | 40° C. |
|---|---|---|---|---|---|
| 10 mM acetate, pH 5.5 145 mM NaCl, 2 mg/mL | none | none | 111.3 | 121.5 | 74.9 |
| 20 mM acetate, pH 5.5 136 mM NaCl, 0.1 mg/mL | none | none | 100.6 | 106.5 | 82.1 |
| 20 mM acetate, pH 5.5 136 mM NaCl, 0.1 mg/mL | none | 0.9% benzyl alc. | 94.2 | 91.3 | 81.6 |
| 20 mM acetate, pH 5.5 136 mM NaCl, 0.1 mg/mL | none | 0.25% phenol | 82.0 | 72.5 | 68.8 |
| 20 mM acetate, pH 5.5 136 mM NaCl, 0.1 mg/mL | 0.01% F68 | none | 92.9 | 79.2 | 80.8 |
| 20 mM acetate, pH 5.5 136 mM NaCl, 0.1 mg/mL | 0.01% F68 | 0.9% benzyl alc. | 92.0 | 80.7 | 83.2 |
| 20 mM acetate, pH 5.5 136 mM NaCl, 0.1 mg/mL | 0.01% F68 | 0.25% phenol | 98.0 | 83.7 | 73.7 |

[a]Calculated as a percentage of assay response for −70° C. control sample at the same storage period.

In the absence of 0.01% F68 in the acetate formulation at pH 5.5, the phenol preserved formulation had less percent protein remaining than both the benzyl alcohol preserved formulation and tie control formulation for all temperatures studied. In the presence of 0.01% F68 in the acetate formulation at pH 5.5, rhNGF in the preserved (benzyl alcohol or phenol) and the control formulation had lost about 20% of its bioactivity at 25 and 40° C. after 9 and 3 months, respectively. These results suggest that phenol and F68 can affect the ability of rhNGF to bind to the NGF receptor on PC-12 cells. Therefore, benzyl alcohol at 0.9% is a better choice of preservative for rhNGF in the acetate formulation containing no surfactant for multi-use purpose.

PC-12 Cell Survival Bioassay

In contrast to the RRA results, the PC-12 cell survival bioassay data in Table 10 show that there was no significant difference in potency of rhNGF in all formulations stored at 5° C. for 12 months and 25° C. for 9 months.

TABLE 10

Stability of current and selected multi-dose liquid formulations for rhNGF determined by bioassay after 12 months at 5° C. and 9 months at 25° C.

| Formulation buffer | Surfactant | Preservative | % rhNGF [a]Remaining 5° C. | 25° C. |
|---|---|---|---|---|
| 10 mM acetate, pH 5.5 145 mM NaCl, 2 mg/mL | none | none | 101.7 | 96.1 |
| 20 mM acetate, pH 5.5 136 mM NaCl, 0.1 mg/mL | none | none | 84.3 | 113.7 |
| 20 mM acetate, pH 5.5 136 mM NaCl, 0.1 mg/mL | none | 0.9% benzyl alc | 102.2 | 97.3 |
| 20 mM acetate, pH 5.5 136 mM NaCl, 0.1 mg/mL | none | 0.25% phenol | 95.3 | 102.1 |
| 20 mM acetate, pH 5.5 136 mM NaCl, 0.1 mg/mL | 0.01% F68 | none | 101.3 | 95.9 |
| 20 mM acetate, pH 5.5 136 mM NaCl, 0.1 mg/mL | 0.01% F68 | 0.9% benzyl alc. | 96.6 | 94.2 |
| 20 mM acetate, pH 5.5 136 mM NaCl, 0.1 mg/mL | 0.01% F68 | 0.25% phenol | 97.8 | 96.4 |

[a]Calculated as a percentage of assay response for −70° C. control sample at the same storage period.

The protein was found to be fully active in all formulations as determined by this bioassay. Therefore, the radioreceptor binding assay is a more stability indicating assay than the cell survival bioassay in determining the bioactivity of rhNGF.

Solutions of all rhNGF formulations were clear and colorless to the naked eyes (Table 11). Particulates were not observed in any of the formulations at all temperatures and timepoints.

TABLE 11 pH and visual clarity of rhNGF formulations after 12 months at 5° C. and 9 months at 25° C.

| Formulation buffer | pH 5° C. | Visual Clarity 5° C. | pH 25° C. | Visual Clarity 25° C. |
|---|---|---|---|---|
| 10 mM acetate, pH 5.5 145 mM NaCl, 2 mg/mL | 5.50 | co/cl | 5.40 | co/cl |
| 20 mM acetate, pH 5.5 136 mM NaCl, 0.1 mg/mL | 5.54 | co/cl | 5.41 | co/cl |
| 20 mM acetate, pH 5.5 136 mM NaCl, 0.1 mg/mL 0.9% benzyl alc. | 5.52 | co/cl | 5.58 | co/cl |
| 20 mM acetate, pH 5.5 136 mM NaCl, 0.1 mg/mL 0.25% phenol | 5.49 | co/cl | 5.60 | co/cl |
| 20 mM acetate, pH 5.5 | 5.47 | co/cl | 5.53 | co/cl |

TABLE 11-continued pH and visual clarity of rhNGF formulations after 12 months at 5° C. and 9 months at 25° C.

| Formulation buffer | pH 5° C. | Visual Clarity 5° C. | pH 25° C. | Visual Clarity 25° C. |
|---|---|---|---|---|
| 136 mM NaCl, 0.1 mg/mL 0.01% F68 | | | | |
| 20 mM acetate, pH 5.5 136 mM NaCl, 0.1 mg/mL 0.01% F68, 0.9% benzyl alc. | 5.42 | co/cl | 5.42 | co/cl |
| 20 mM acetate, pH 5.5 136 mM NaCl, 0.1 mg/mL 0.01% F68, 0.25% phenol | 5.48 | co/cl | 5.41 | co/cl | co/cl = colorless and clear pH Results rhNGF formulated in 10 mM acetate, 142 mM sodium chloride at either pH 5.0 or pH 5.8 had an increase in pH by 0.2 units during the stability study. The multi-dose formulations and their control formulations used in this study were formulated in 20 mM acetate at pH 5.5 which should provide a higher buffer capacity to prevent pH change. Table 11 shows that pH remained unchange for all formulations studied.

Preservative Effectiveness Test

After 6 months of stability study, the most stable multi-dose formulation for rhNGF which consists of 0.1 mg/mL rhNGF in 20 mM acetate at pH 5.5, 136 mM sodium chloride, and 0.9% benzyl alcohol was submitted for preservative efficacy testing. This lead formulation passed both the USP and EP (criteria A and B) after 6 months storage at 5° C.

Circular Dichroism (CD) Analysis

Figure 16:
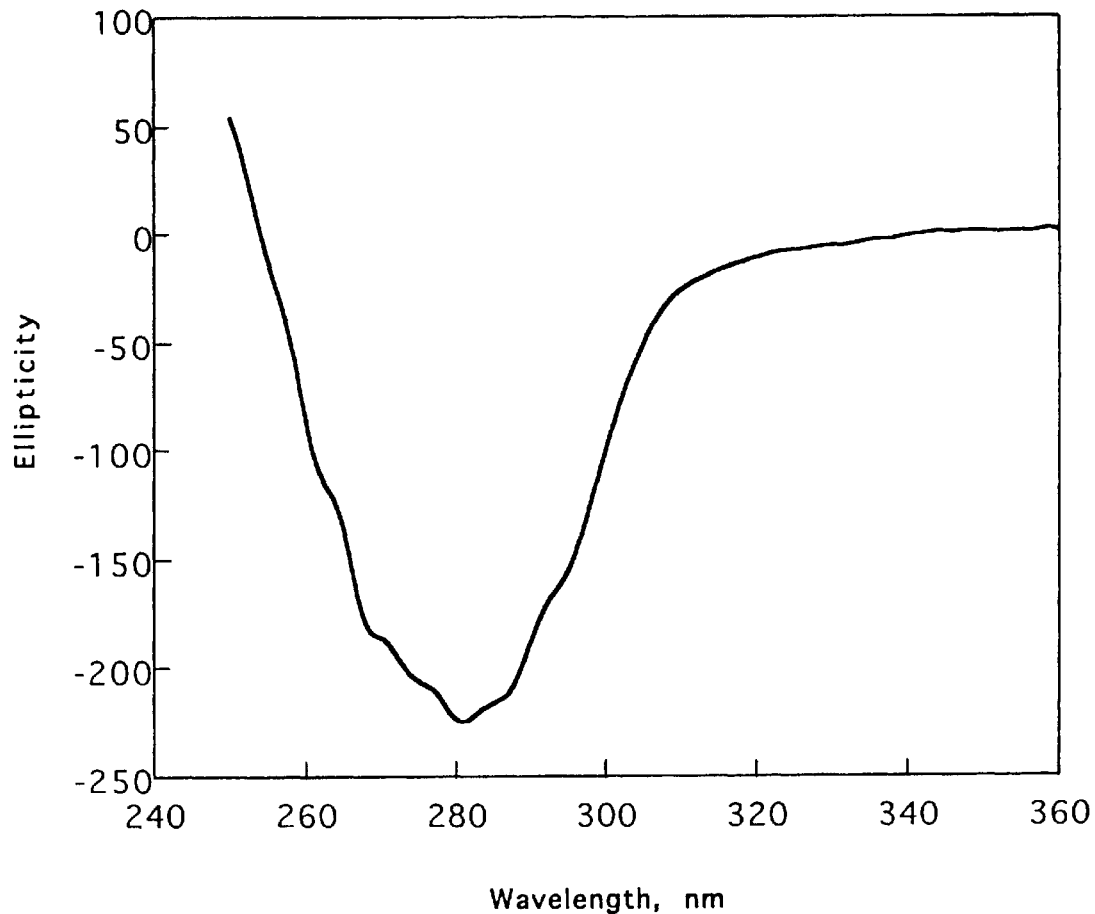
FIG. 16 depicts near UV CD spectrum of rhNGF in 10 mM acetate, 136 mM NaCl, pH 5.5.
Figure 17:
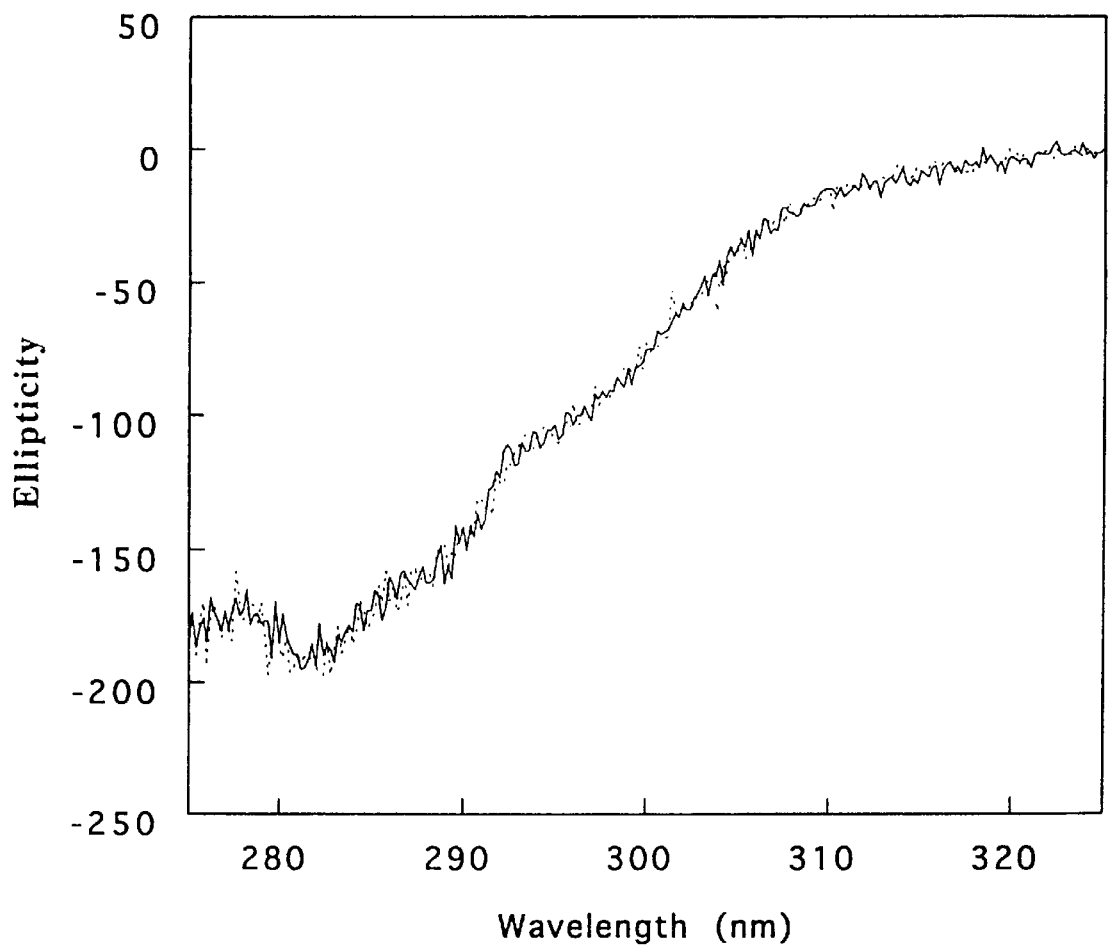
FIG. 17 depicts a comparison of near-UV CD spectra of rhNGF in the presence (solid line) and absence (dotted line) of 0.9% benzyl alcohol in 20 mM acetate at pH 5.5 and 136 mM NaCl after 24 hours at 25 degrees C.

The presence of 0.9% benzyl alcohol in various liquid interferon-gamma(rhIFN-g) formulations induces loss in circular dichroism signals in the near-UV region. The near-UV CD signal of rhIFN-g disappeared within 24 hours, indicating that there was a change in tertiary structure of the protein due to the presence of benzyl alcohol. However, this phenomenon was not observed in the rhNGF formulation preserved with 0.9% benzyl alcohol. After 24 hours of the addition of the preservative, the near-UV CD spectrum remained unchange, suggesting that there is no interaction between rhNGF and benzyl alcohol in the acetate formation at pH 5.5. FIG. 16 shows the near-UV CD spectrum of rhNGF, and FIG. 17 compares the near-UV CD spectra of rhNGF in the presence and absence of benzyl alcohol after 24 hours at 25° C. Due to the interference of benzyl alcohol at wavelength below 275 nm, CD spectrum of rhNGF was scanned from 325 nm to 275 nm when the sample contained the preservative.

Stresses Testing Stability

1. Agitation Studies

Shaker studies were performed to determine whether it is necessary to add surfactant (F68) in the rhNGF multi-dose formulations at low protein concentration such as 0.1 mg/mL in order to prevent protein aggregation and maintain visual clarity of the solutions during agitation. The Data of Table 12 show that rhNGF at 0.1 mg/mL in the 20 mM acetate formulation at pH 5.5 (with or without preservative) is quite stable to mechanical disruption such as shaking. This suggests that surfactant is not required in formulating rhNGF at 0.1 mg/mL as multi-dose liquid form for stability purpose.

TABLE 12

Effect of agitation on stability of rhNGF multi-dose liquid formulations. Samples were shaken at 80 rpm for 6 and 24 hours at room temperature.

| Formulation | Hours RRA | % Monomer (SEC) | % Iso-Asp (RP-HPLC) | % NGF (RP-HPLC) | ELISA (mg/mL) | (mg/mL) |
|---|---|---|---|---|---|---|
| 1 | 6 | 0 | 0.6 | 101.6 | 0.1 | 0.11 |
|   | 24 | 0.4 | 0.5 | 101.7 | 0.09 | 0.11 |
| 2 | 6 | 0 | 0.8 | 103.6 | 0.09 | 0.11 |
|   | 24 | 0 | 0.7 | 100.8 | 0.09 | 0.10 |
| 3 | 6 | 0 | 0.6 | 101.3 | 0.09 | 0.10 |
|   | 24 | 0 | 0.6 | 101.0 | 0.09 | 0.10 |
| 4 | 6 | 0 | 0.6 | 100.8 | 0.09 | 0.10 |
|   | 24 | 0 | 0.7 | 101.0 | 0.09 | 0.10 |

Formulations:
1. 2 mg/mL, 10 mM acetate pH 5.5, 145 mM NaCl.
2. 0.1 mg/mL, 20 mM acetate pH 5.5, 136 mM NaCl.
3. 0.1 mg/mL, 20 mM acetate pH 5.5, 136 mM NaCl, 0.9% benzyl alcohol.
4. 0.1 mg/mL, 20 mM acetate pH 5.5, 136 mM NaCl, 0.25% phenol.

2. Freezing-Thawing Studies

Results on the effect of freezing and thawing on stability of 0.1 mg/mL rhNGF multi-dose liquid formulations are presented in Table 13.

TABLE 13

Effect of freeze-thaw on stability of rhNGF multi-dose liquid formulations.

| Formulation | Freeze -70° C. RRA Thaw 5° C. | % Aggregate (SEC) | % Iso-Asp (RP-HPLC) | % NGF (RP-HPLC) | ELISA (mg/mL) | (mg/mL) |
|---|---|---|---|---|---|---|
| 1 | 3 cycles | 0 | 0.9 | 102.1 | 0.09 | 0.10 |
| 2 | 3 cycles | 0 | 0.4 | 102.1 | 0.08 | 0.10 |
| 3 | 3 cycles | 0 | 0.8 | 101.3 | 0.09 | 0.11 |
| 4 | 3 cycles | 0 | 0.5 | 101.8 | 0.09 | 0.10 |

Formulations:
1. 2 mg/mL, 10 mM acetate pH 5.5, 145 mM NaCl.
2. 0.1 mg/mL, 20 mM acetate pH 5.5, 136 mM NaCl.
3. 0.1 mg/mL, 20 mM acetate pH 5.5, 136 mM NaCl, 0.9% benzyl alcohol.
4. 0.1 mg/mL, 20 mM acetate pH 5.5, 136 mM NaCl, 0.25% phenol.

After 3 cycles of freezing and thawing, the 0.1 mg/mL rhNGF in the 20 mM acetate formulation at pH 5.5 as control and the two multi-dose formulations containing either 0.9% benzyl alcohol or 0.25% phenol did not show any loss in stability of the protein. They are as stable as the current 2 mg/mL rhNGF liquid formulation after 3 cycles of freezing and thawing between −70 and 5° C.

3. Light Compatibility Studies

Table 14 summarizes the effect of light on stability of rhNGF in the current 2 mg/mL formulation, the 0.1 mg/mL rhNGF control formulation, and the benzyl alcohol or phenol preserved 0.1 mg/mL rhNGF formulations.

TABLE 14

Effect of light on stability of rhNGF multi-dose liquid formulations. Samples were illuminated at a light intensity of 20,000 lux at 28° C.

| Formulation | Conc. RRA | Storage (mg/mL) | Weeks Condition | % Aggregate (SEC) | ELISA (mg/mL) | (mg/mL) |
|---|---|---|---|---|---|---|
| 10 mM acetate pH 5.5 145 mM NaCl | 2 | Dark | 2 | 0 | 2.20 | 2.00 |
| | | | 5 | 0.3 | 2.20 | 2.00 |
| 20 mM acetate pH 5.5 136 mM NaCl | 0.1 | Dark | 2 | 0 | 0.10 | 0.11 |
| | | | 5 | 0 | 0.09 | 0.10 |
| 20 mM acetate pH 5.5 136 mM NaCl, 0.9% benzyl alcohol | 0.1 | Dark | 2 | 0 | 0.10 | 0.11 |
| | | | 5 | 0 | 0.10 | 0.10 |
| 20 mM acetate pH 5.5 136 mM NaCl, 0.25% phenol | 0.1 | Dark | 2 | 0 | 0.10 | 0.10 |
| | | | 5 | 0.2 | 0.10 | 0.10 |
| 10 mM acetate pH 5.5 145 mM NaCl | 2 | Light | 2 | 0.4 | 2.20 | 2.40 |
| | | | 5 | 1.6 | 2.00 | 1.80 |
| 20 mM acetate pH 5.5 136 mM NaCl | 0.1 | Light | 2 | 0 | 0.10 | 0.10 |
| | | | 5 | 0.3 | 0.09 | 0.09 |
| 20 mM acetate pH 5.5 136 mM NaCl, 0.9% benzyl alcohol | 0.1 | Light | 2 | 0 | 0.10 | 0.10 |
| | | | 5 | 0.2 | 0.09 | 0.09 |
| 20 mM acetate pH 5.5 136 mM NaCl, 0.25% phenol | 0.1 | Light | 2 | 0.7 | 0.09 | 0.10 |
| | | | 5 | 12.1 | 0.07 | 0.04 |

After storage for 2 weeks in the light box, there was no significant loss in stability of the protein in all formulations studied. However, after 5 weeks of storage in the light box, SE-HPLC indicated an increase in aggregate formation occurred in the current formulation (1.6%). Aggregate formation was even more pronounced in the phenol preserved formulation (12.1%) after 5 weeks exposure to light. There was also a 30% loss in protein concentration and 60% in bioactivity in the light exposed phenol containing formulation as determined by ELISA and RRA, respectively. Both benzyl alcohol preserved formulation and the 0.1 mg/mL rhNGF control formulation were stable after exposure to light for 5 weeks. All control vials wrapped with aluminum foil were stable after 5 weeks of storage in the light box. These results suggest that rhNGF is more sensitive to light at higher protein concentration (2 mg/mL) than at lower protein concentration (0.1 mg/mL) in the acetate formulation at pH 5.5. In the presence of phenol, rhNGF degrades more faster upon light exposure.

All 0.1 mg/mL rhNGF multi-dose liquid formation at pH 5.5 are stable at 5° C. for 12 months. At 25° C., the formulations (with or without F68) using 0.25% phenol as preservative were less stable than the formulations using 0.9% benzyl alcohol.

0.1 mg/mL rhNGF Formulations at pH 5.5 containing surfactant (F68) are as stable as the formulations containing no surfactant.

The lead multi-dose formulation for rhNGF is 0.1 mg/mL protein in 20 mM acetate, pH 5.5, 136 mM NaCl and 0.9% benzyl alcohol filled in 3 cc vial with 1.8 mL filled. This formulation passed both the USP and EP preservative efficacy testing after 6 month storage at 5° C.

rhNGF at 0.1 mg/mL formulated in 20 mM acetate, 136 mM NaCl pH 5.5 is as stable as the current 2 mg/mL liquid formulation.

Agitation has no effect on stability of rhNGF, with regardless to protein concentration or excipient in the formulation.

rhNGF is more stable in the dark than in the light especially if the formulation contains phenol as preservative.

rhNGF at 2 mg/mL in the current formulation and at 0.1 mg/mL in the multi-dose liquid formulations can undergo at least 3 cycles of freezing (−70° C.) and thawing (5° C.) without any adverse effect on the stability of the protein.

Cited References

1. H. Thoenen and Y. A. Barde. Physiology of nerve growth factor. Physiol. Rev. 60:1284– 1335 (1980).
2. S. C. Apfel, R. B. Lipton, J. C. Arezzo, and J. A. Kessler. Nerve growth factor prevents toxic neuropathy in mice. Ann. Neurol. 28:87–90 (1991).
3. S. C. Apfel, J. C. Arezzo, L. A. Lipson, and J. A. Kessler. Nerve growth factor prevents experimental cisplatin neuropathy. Ann. Neurol. 31:76–80 (1992).
4. B. G. Petty, D. R. Cornblath, B. T. Adornato, V. Chaudhry, C. Flexner, M. Wachsman, D. Sinicropi, L. E. Burton, S. J. Peroutka. The effect of systemically administered recombinant human nerve growth factor in healthy human subjects. Ann. Neurol. 36:244–246 (1994).
5. N. Q. McDonald, R. Lapatto, J. Murray-Rust, J. Gunning, A. Wlodawer, and T. L. Blundell. New protein fold revealed by a 2.3 Å resolution crystal structure of nerve growth factor. Nature 354:411–414 (1991).
6. M. A. Bothwell and E. M. Shooter. Dissociation equilibrium constant of b nerve growth factor. J. Biol. Chem. 252:8532–8536 (1977).
7. D. E. Timm, P. L. de Haseth, and K. E. Neet. Comparative equilibrium denaturation of the neurotrophins: nerve growth factor, brain-derived neurotrophic factor, neurotrophin 3, and neurotrophin 4/5. Biochem. 33:4667–4676 (1994).
8. C. H. Schmelzer, L. E. Burton, W.-P. Chan, E. Martin, C. Gorman, E. Canova-Davis, V. T. Ling, M. B. Sliwkowski, G. McCray, J. A. Briggs, T. H. Nguyen, and G. Polastri. Biochemical characterization of recombinant human nerve growth factor. J. Neurochem. 59:1675–1683 (1992).
9. J. B. Moore, and E. M. Shooter. The use of hybrid molecules in a study of the equilibrium between nerve growth factor monomers and dimers. Neurobiol. 5:369–381 (1975).
10. L. A. Greene. A quantitative bioassay for nerve growth factor activity employing a clonal pheochromocytoma cell line. Brain Res. 133:350–353 (1977).

11. K. Reed and S. Yalkowsky. Lysis of human red blood cells in the presence of various cosolvents. III. The relationship between hemolytic potential and structure. J. Parenter. Sci. Technol. 41:37–39 (1987)
12. D. E. Timm and K. E. Neet. Equilibrium denaturation studies of mouse b-nerve growth factor. Prot. Sci. 1:236–244 (1992).
13. E. Canova-Davis, V. Ling, M. Eng, and S. Skieresz. Amino-terminal serine to glycine post-translational modification observed in nerve growth factor biosynthesized in Chinese hamster ovary cells. In Peptides: Chemistry, Structure and Biology, Escom Science Publishers, Leiden, The Netherlands, pp. (1993). (Proceedings of the Thirteenth American Peptide Symposium, Edmonton, Alberta, Canada, Jun. 20–25, 1993).
14. L. R. De Young, J. A. Briggs, and M. F. Powell Temperature and pH dependence of recombinant human nerve growth factor dimer dissociation Biophys. J. 66:A401 (1994)

What is claimed is:

1. A composition produced by the process comprising formulating an aqueous liquid composition consisting essentially of human nerve growth factor (NGF) and a pharmaceutically acceptable acetate-containing buffer wherein the composition is formulated with 0.1 mg/ml NGF, 20 mM sodium acetate, 136 mM sodium chloride, 0.9% (v/v) benzyl alcohol, at pH of 5.5.

* * * * *